United States Patent
Takebe et al.

(10) Patent No.: US 10,653,378 B2
(45) Date of Patent: May 19, 2020

(54) IMAGE RETRIEVAL APPARATUS AND IMAGE RETRIEVAL METHOD

(71) Applicant: FUJITSU LIMITED, Kawasaki-shi, Kanagawa (JP)

(72) Inventors: Hiroaki Takebe, Kawasaki (JP); Yasutaka Moriwaki, Kawasaki (JP); Masahiko Sugimura, Kawasaki (JP); Susumu Endo, Kawasaki (JP); Takayuki Baba, Kawasaki (JP); Yusuke Uehara, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 107 days.

(21) Appl. No.: 15/798,115

(22) Filed: Oct. 30, 2017

(65) Prior Publication Data
US 2018/0125443 A1 May 10, 2018

(30) Foreign Application Priority Data

Nov. 7, 2016 (JP) .................................. 2016-217182

(51) Int. Cl.
*G06K 9/62* (2006.01)
*G06T 7/33* (2017.01)
(Continued)

(52) U.S. Cl.
CPC ............ *A61B 6/5217* (2013.01); *A61B 6/032* (2013.01); *A61B 6/461* (2013.01); *A61B 6/50* (2013.01);
(Continued)

(58) Field of Classification Search
CPC .......................................... G06T 2207/30061
See application file for complete search history.

(56) References Cited

U.S. PATENT DOCUMENTS

2002/0051515 A1* 5/2002 Saotome ................ G03B 42/02
378/95
2006/0025671 A1* 2/2006 Kusunoki ............. G06T 7/0012
600/407
(Continued)

FOREIGN PATENT DOCUMENTS

JP 2006-34585 2/2006
JP 2007-275216 10/2007
(Continued)

OTHER PUBLICATIONS

Awais Mansoor et al.: "Segmentation and Image Analysis of Abnormal Lungs at CT: Current Approaches, Challenges, and Future Trends", Radiographics., vol. 35, No. 4, Jul. 1, 2015, pp. 1056-1076, XP055329729.
(Continued)

*Primary Examiner* — Gandhi Thirugnanam
(74) *Attorney, Agent, or Firm* — Fujitsu Patent Center

(57) ABSTRACT

An image retrieval apparatus that retrieves a candidate medical image in diagnosis of diffuse lung disease based on a position of an abnormal shadow in an organ region in a target medical image, the apparatus includes a memory, and a processor coupled to the memory and configured to map the organ region in the target medical image to an image having a predetermined shape to make it identifiable whether the abnormal shadow is distributed over a first portion in the organ region or a second portion in the organ region, occurrence portions of the abnormal shadow within the first portion and the second portion are organizationally different, and calculate a position of the abnormal shadow after the mapping in the image having the predetermined shape.

9 Claims, 20 Drawing Sheets

(51) Int. Cl.
*G06T 7/73* (2017.01)
*G06T 7/11* (2017.01)
*G06T 7/174* (2017.01)
*G06T 7/00* (2017.01)
*G06K 9/46* (2006.01)
*A61B 6/00* (2006.01)
*A61B 6/03* (2006.01)
*A61B 5/08* (2006.01)

(52) U.S. Cl.
CPC .......... *G06K 9/6207* (2013.01); *G06T 7/0014* (2013.01); *G06T 7/11* (2017.01); *G06T 7/174* (2017.01); *G06T 7/337* (2017.01); *G06T 7/74* (2017.01); *A61B 5/08* (2013.01); *G06K 9/4604* (2013.01); *G06K 2209/051* (2013.01); *G06T 2207/10081* (2013.01); *G06T 2207/30061* (2013.01)

(56) References Cited

U.S. PATENT DOCUMENTS

| | | | | |
|---|---|---|---|---|
| 2008/0049991 | A1* | 2/2008 | Gering | G06T 19/00 382/128 |
| 2008/0253631 | A1* | 10/2008 | Oosawa | G16H 15/00 382/128 |
| 2009/0118614 | A1* | 5/2009 | Sendai | A61B 5/0077 600/437 |
| 2013/0034282 | A1* | 2/2013 | Kaufman | G06T 7/0014 382/128 |
| 2013/0169640 | A1* | 7/2013 | Sakuragi | G06T 19/20 345/424 |
| 2014/0257114 | A1* | 9/2014 | Hirota | A61B 1/041 600/476 |
| 2018/0125443 | A1* | 5/2018 | Takebe | G06T 7/74 |

FOREIGN PATENT DOCUMENTS

| | | |
|---|---|---|
| JP | 2007-286945 | 11/2007 |
| JP | 2009-45121 | 3/2009 |

OTHER PUBLICATIONS

Mehrdad Alemzadeh: "Pattern Recognition and Classification of CT Images of Diffuse Lung Diseases Using Feature Extraction and Artificial Neural Networks", a Thesis submitted to the School of Graduate Studies at McMaster University, Mar. 1, 2016, XP055494553.
EESR—Extended European Search Report dated Aug. 10, 2018 in corresponding European Patent Application No. 17198587.2.

* cited by examiner

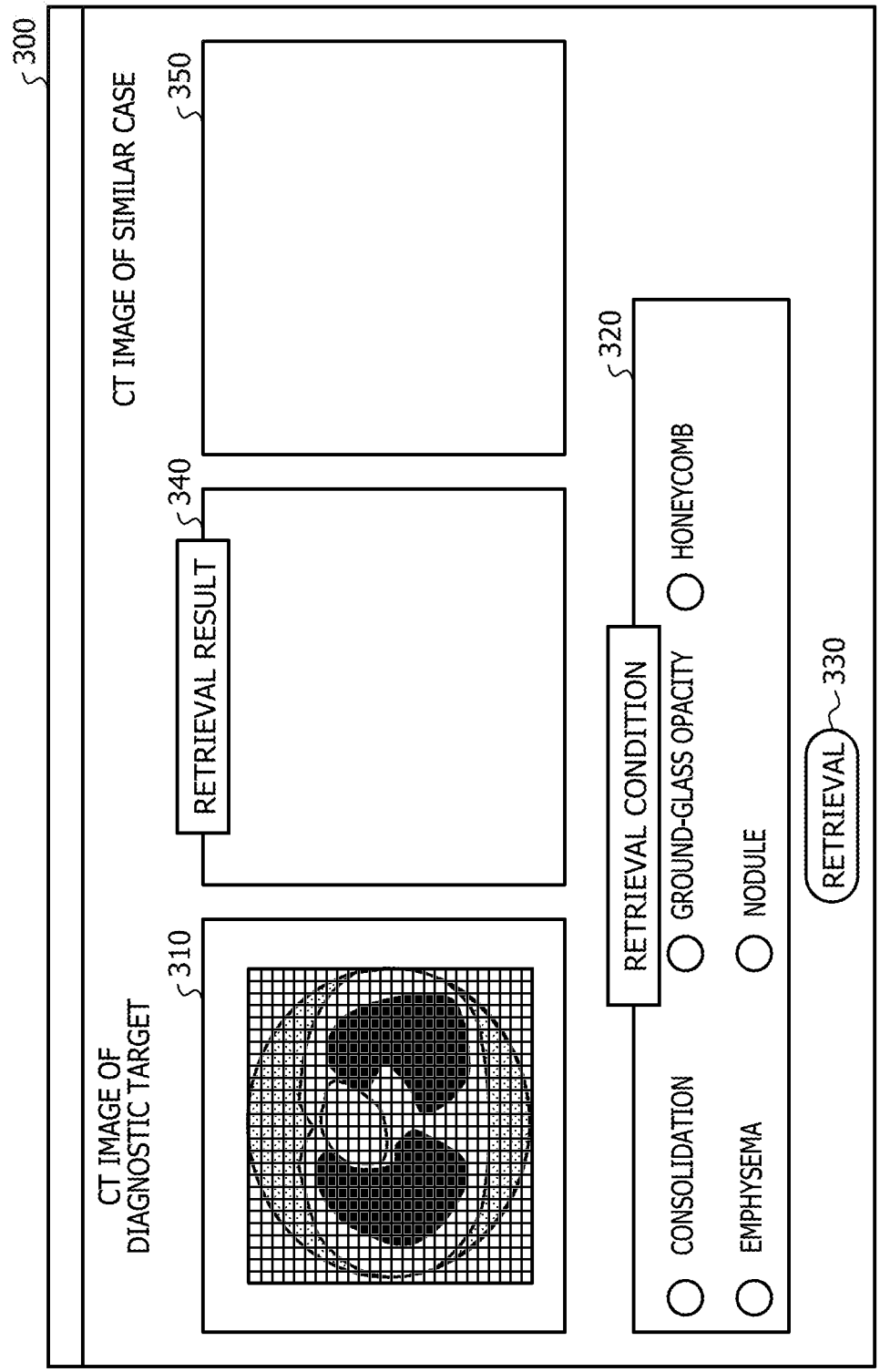

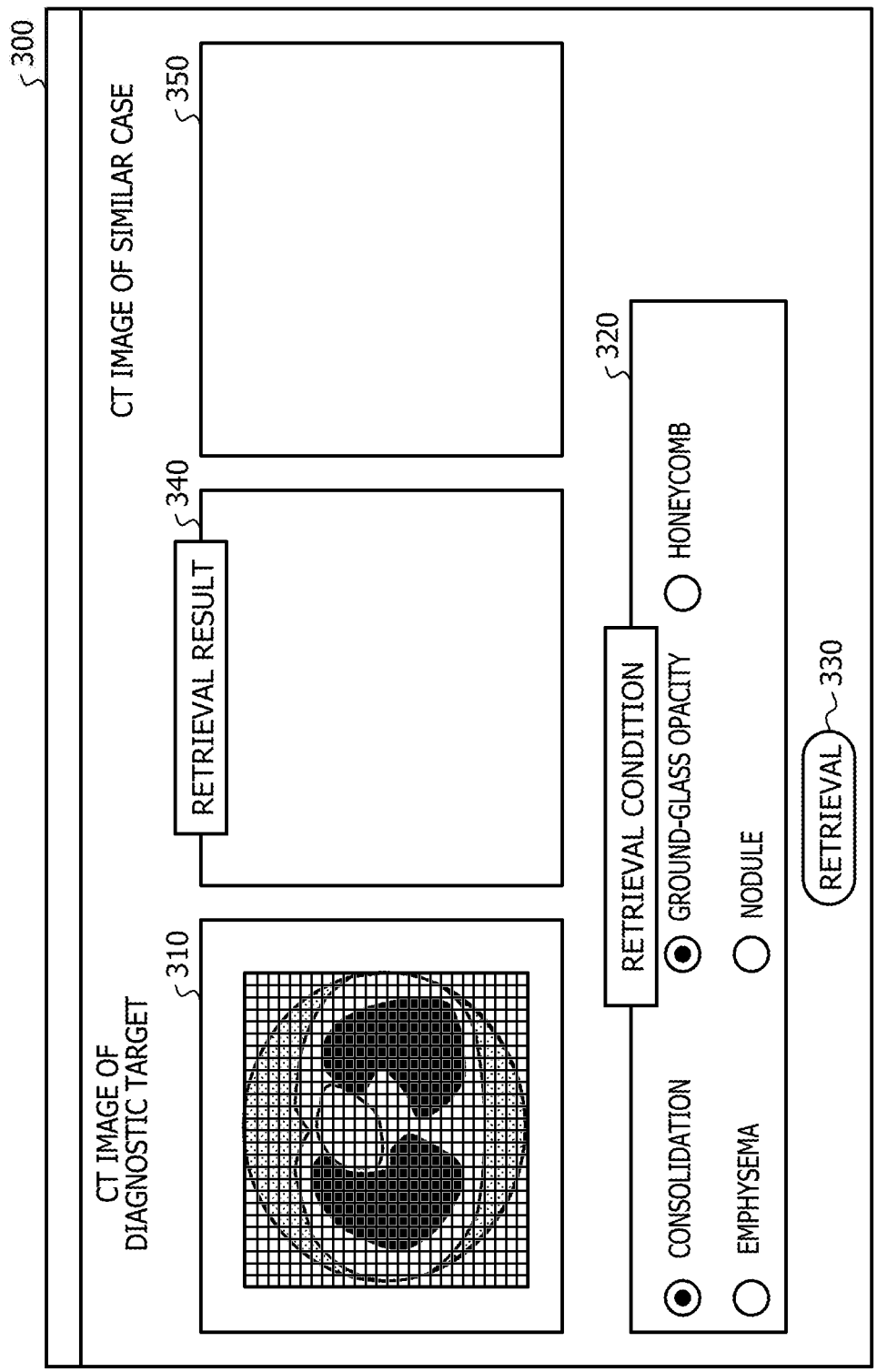

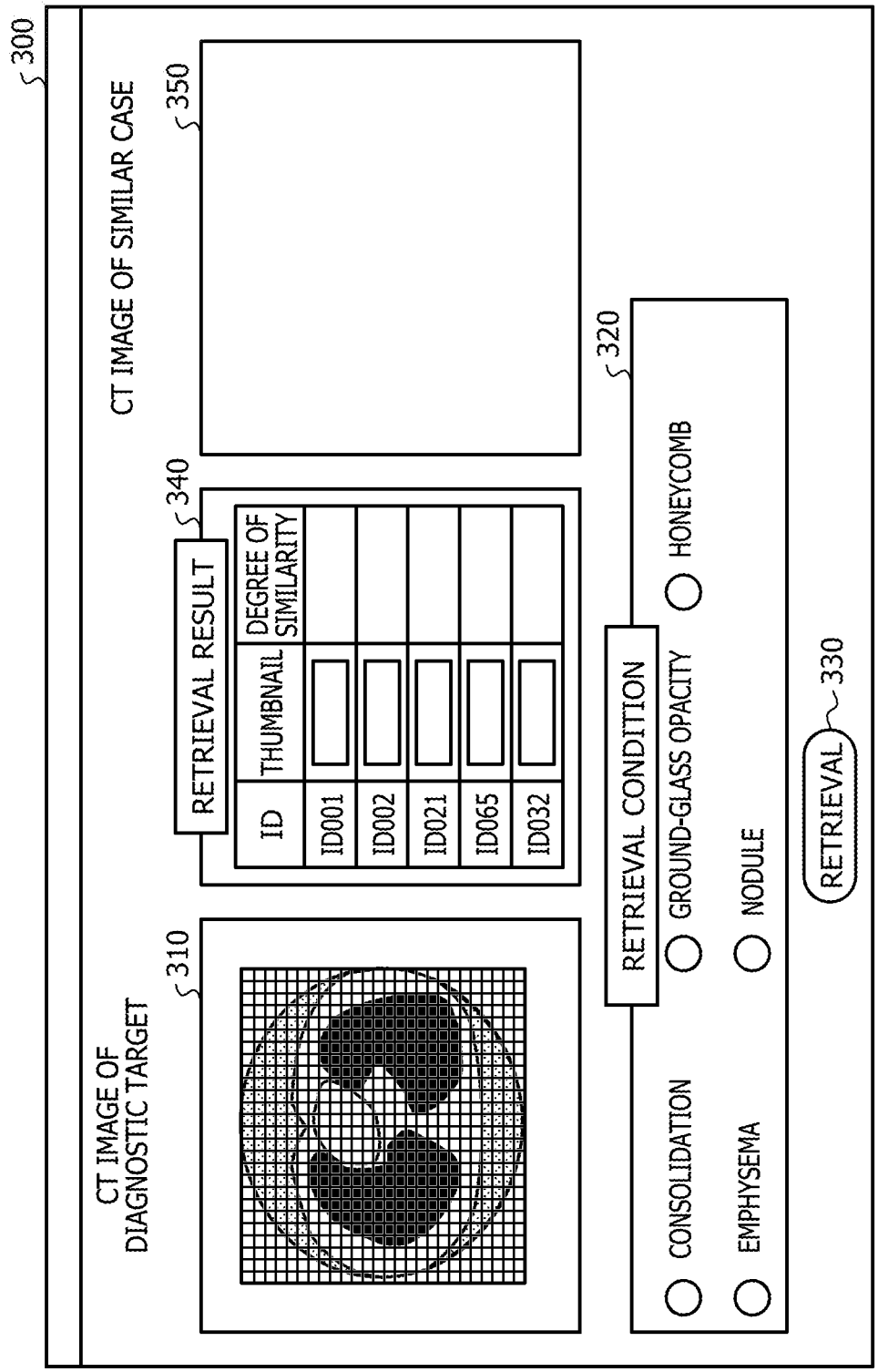

FIG. 5

| CHARACTERISTIC QUANTITY INFORMATION ||||| 500 |
|---|---|---|---|---|
| ID | THUMBNAIL IMAGE | TYPE | NUMBER OF PIECES | DISTRIBUTION CHARACTERISTIC QUANTITY |
| 001 | image001 | ABNORMAL SHADOW 1 | 5 | $(x_{11},y_{11}), (x_{12},y_{12}), \cdots (x_{15},y_{15})$ |
| | | ABNORMAL SHADOW 1 | 3 | $(x_{21},y_{21}), (x_{22},y_{22}), (x_{23},y_{23})$ |
| | | ABNORMAL SHADOW 1 | 6 | $(x_{31},y_{31}), (x_{32},y_{32}), \cdots (x_{36},y_{36})$ |
| | | ABNORMAL SHADOW 1 | 0 | – |
| | | ABNORMAL SHADOW 1 | 9 | $(x_{51},y_{51}), (x_{52},y_{52}), \cdots (x_{59},y_{59})$ |
| | | NORMAL | 300 | ⋯ |
| | | | | |

FIG. 6

| ID | IMAGE | CT IMAGE INFORMATION | | | | DIAGNOSTIC RESULT | DIAGNOSTICIAN |
|---|---|---|---|---|---|---|---|
| | | PATIENT INFORMATION | | | | | |
| | | PATIENT ID | NAME | AGE | SEX | | |
| 001 | IMAGE001 | | | | | | |
| 002 | IMAGE002 | | | | | | |
| 003 | IMAGE003 | | | | | | |
| 004 | IMAGE004 | | | | | | |

600

810   830        820

840          850

FIG. 13
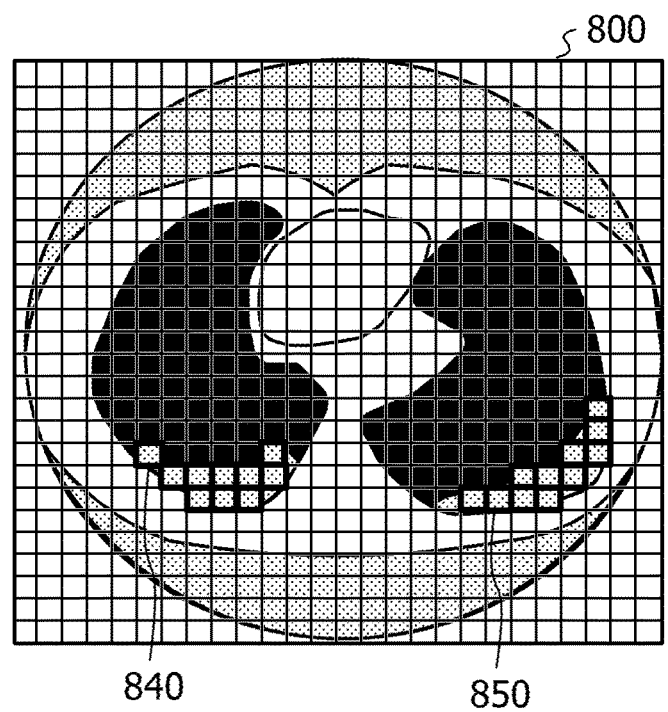
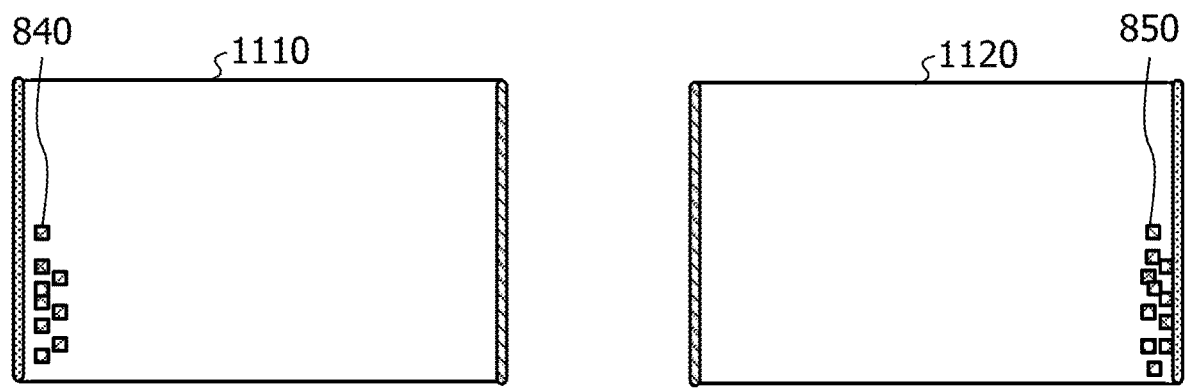

IMAGE RETRIEVAL APPARATUS AND IMAGE RETRIEVAL METHOD

CROSS-REFERENCE TO RELATED APPLICATION

This application is based upon and claims the benefit of priority of the prior Japanese Patent Application No. 2016-217182, filed on Nov. 7, 2016, the entire contents of which are incorporated herein by reference.

FIELD

The embodiments discussed herein are related to an image retrieval apparatus and an image retrieval method in a similar case.

BACKGROUND

Conventionally, in medical facilities, comparative reading has been performed, in which a diagnosis is made with reference to disease cases (similar disease cases) in the past similar to the disease case of a medical image which is a diagnostic target, and a similar case image retrieval apparatus is utilized as an apparatus that retrieves medical images of similar disease cases.

Diffuse lung disease is one of the cases for which it is difficult for a diagnostic radiologist to make a diagnosis when performing comparative reading. Diffuse lung disease is a disease that causes the function in an extensive region of the lung to be impaired and an impaired portion appears as an abnormal shadow, and the disease has characteristics that the shape and distribution of the abnormal shadow are complicated and diverse. For this reason, diagnosis of diffuse lung disease is more difficult than cancer of a solitary pulmonary nodule, and it is important to retrieve medical images of similar disease cases.

To cope with this, for instance, Japanese Laid-open Patent Publication Nos. 2009-45121, 2007-275216, and 2007-286945 propose a method to retrieving a medical image of a similar case based on an image characteristic quantity which is calculated for the shape of abnormal shadows in regions in a diagnostic target medical image. Furthermore, Japanese Laid-open Patent Publication No. 2006-34585 proposes a method to retrieving a medical image having abnormal shadows at positions similar to the positions of abnormal shadows in a diagnostic target medical image.

SUMMARY

According to an aspect of the invention, an image retrieval apparatus that retrieves a candidate medical image in diagnosis of diffuse lung disease based on a position of an abnormal shadow in an organ region in a target medical image, the apparatus includes a memory, and a processor coupled to the memory and configured to map the organ region in the target medical image to an image having a predetermined shape to make it identifiable whether the abnormal shadow is distributed over a first portion in the organ region or a second portion in the organ region, occurrence portions of the abnormal shadow within the first portion and the second portion are organizationally different, and calculate a position of the abnormal shadow after the mapping in the image having the predetermined shape.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIGS. 3A and 3B are each a first diagram illustrating an example display screen of the similar case image retrieval apparatus;

FIGS. 4A and 4B are each a second diagram illustrating an example display screen of the similar case image retrieval apparatus;

FIG. 5 is a table illustrating example characteristic quantity information;

FIG. 6 is a table illustrating example CT image information;

FIG. 13 is a diagram illustrating an example of distribution characteristic quantity calculation processing performed by the distribution conversion section;

DESCRIPTION OF EMBODIMENTS

In the case of diffuse lung disease, a diagnostic radiologist or the like often makes a diagnosis in consideration of not only the characteristics of the shape of an abnormal shadow in each of areas in a medical image, but also the characteristics of the distribution of abnormal shadows in the whole lung regions. For this reason, it is difficult to retrieve a medical image of a similar disease case by a system of retrieving a medical image based on the image characteristic quantity of each abnormal shadow as in Japanese Laid-open Patent Publication Nos. 2009-45121, 2007-275216, and 2007-286945.

In contrast, in Japanese Laid-open Patent Publication No. 2006-34585, a medical image is retrieved in consideration of the position of an abnormal shadow in a diagnostic target medical image. However, in the case of diffuse lung disease, its characteristics include distribution of abnormal shadows over an extensive region of the lung, and even when the positions of abnormal shadows are not similar between cases, the cases may be similar, or conversely even when the positions of abnormal shadows are similar between cases, the cases may not be similar. In short, it is difficult to retrieve a medical image of a similar case even in consideration of the similarity/dissimilarity between the positions of abnormal shadows.

An aspect of the present disclosure aims to provide a retrieval technology capable of retrieving a medical image of a similar case for diffuse lung disease.

Hereinafter, embodiments will be described with reference to the accompanying drawings. It is to be noted that in the description and drawings, components having substantially the same functional configuration are labeled with the same symbol to omit a redundant description.

First Embodiment

System Configuration of CT Image Processing System

Figure 1:
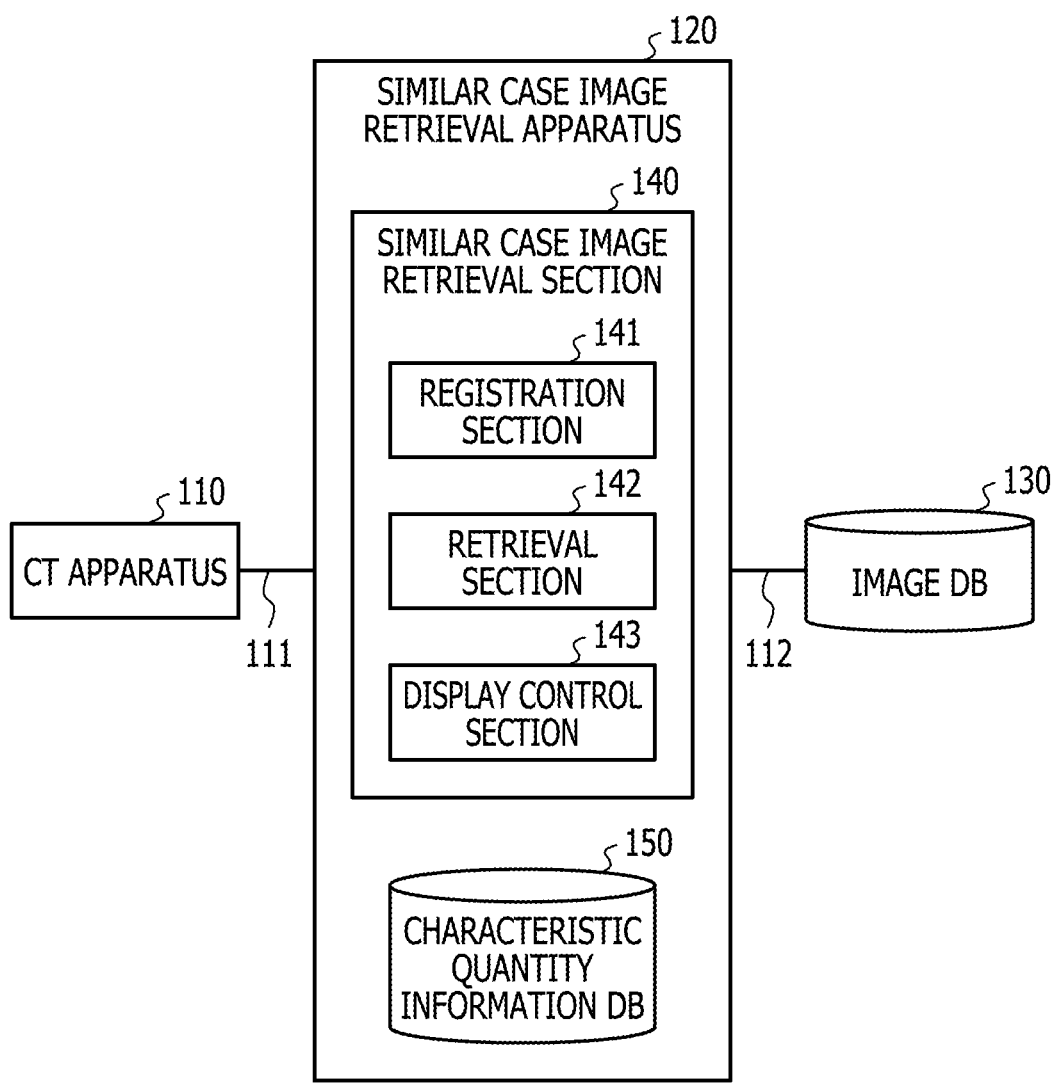
FIG. 1 is a diagram illustrating an example CT image processing system.

First, a CT image processing system including a similar case image retrieval apparatus in a first embodiment will be described. FIG. 1 is a diagram illustrating an example CT image processing system.

A CT image processing system 100 has a computed tomography (CT) apparatus 110, a similar case image retrieval apparatus 120, and an image database (hereinafter database is abbreviated as DB) 130. The CT apparatus 110 and the similar case image retrieval apparatus 120 are coupled via a wire 111, various types of data are transmitted and received between both apparatuses. In addition, the similar case image retrieval apparatus 120 and the image DB 130 are coupled via a wire 112, various types of data are also transmitted and received between both apparatuses.

The CT apparatus 110 generates CT images that are slice images of a patient, as medical images by scanning the body of the patient utilizing radioactive rays, and processing the images using a computer (hereinafter such processing is referred to as "capturing CT images"). The CT apparatus 110 transmits the captured CT images to the similar case image retrieval apparatus 120.

In the similar case image retrieval apparatus 120, a similar case image retrieval program is installed, and the similar case image retrieval apparatus 120 functions as a similar case image retrieval section 140 by execution of the similar case image retrieval program by a computer.

The similar case image retrieval section 140 has a registration section 141, a retrieval section 142, and a display control section 143. The registration section 141 stores a CT image captured by the CT apparatus 110 in the image DB 130, calculates a distribution characteristic quantity (the details will be described later) for the CT image, and stores the distribution characteristic quantity in a characteristic quantity information DB 150.

The retrieval section 142 calculates a distribution characteristic quantity for the diagnostic target CT image captured by the CT apparatus 110. In addition, the retrieval section 142 retrieves a distribution characteristic quantity similar to the calculated distribution characteristic quantity from retrieval targets in the characteristic quantity information DB 150, thereby retrieving a CT image of a disease case similar to the disease case of the CT image of a diagnostic target. In addition, the retrieval section 142 notifies the display control section 143 of an identifier that identifies the retrieved CT image.

The display control section 143 displays a display screen for a diagnostic radiologist or the like to perform comparative reading for a CT image of a diagnostic target. The display screen provides a display function for displaying a CT image of a diagnostic target. Also, the display screen provides an instruction function for a diagnostic radiologist or the like to retrieve a CT image of a disease case similar to the disease case of the CT image of a diagnostic target. Furthermore, the display screen provides a comparison display function for displaying a CT image read from the image DB 130 in comparison with a CT image of a diagnostic target based on the notification from the retrieval section 142.

The image DB 130 stores a CT image captured by the CT apparatus 110. In addition, the image DB 130 transmits the stored CT image to the similar case image retrieval apparatus 120 based on an instruction from the similar case image retrieval apparatus 120.

Hardware Configuration of Similar Case Image Retrieval Apparatus

Figure 2:
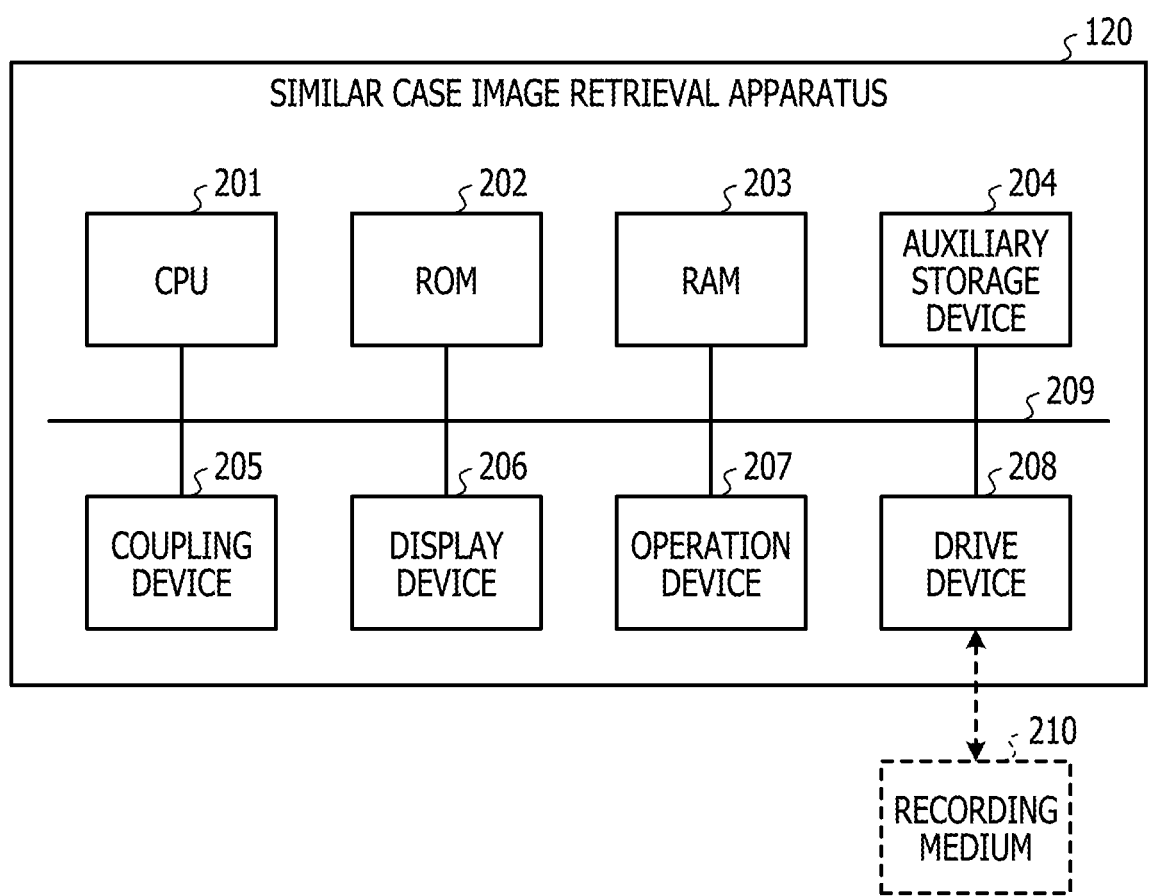
FIG. 2 is a diagram illustrating the hardware configuration of a similar case image retrieval apparatus.

Next, the hardware configuration of the similar case image retrieval apparatus 120 will be described. FIG. 2 is a diagram illustrating the hardware configuration of the similar case image retrieval apparatus. As illustrated in FIG. 2, the similar case image retrieval apparatus 120 includes a central processing unit (CPU) 201, a read only memory (ROM) 202, and a random access memory (RAM) 203. The CPU 201, the ROM 202 and the RAM 203 form what is called a computer.

In addition, the similar case image retrieval apparatus 120 includes an auxiliary storage device 204, a coupling device 205, a display device 206, an operation device 207, and a drive device 208. It is to be noted that each hardware of the similar case image retrieval apparatus 120 is coupled to each other via a bus 209.

The CPU 201 executes various programs (for instance, the similar case image retrieval program) stored in the auxiliary storage device 204.

The ROM 202 is a non-volatile memory. The ROM 202 serves as a main memory that stores various programs and data requested for the CPU 201 to execute the various programs stored in the auxiliary storage device 204. Specifically, the ROM 202 stores boot programs such as a basic input/output system (BIOS) and an extensible firmware interface (EFI).

The RAM 203 is volatile memory and includes a dynamic random access memory (DRAM), and a static random access memory (SRAM). The RAM 203 is a main memory that provides a working area which is allocated when the various programs stored in the auxiliary storage device 204 are executed by the CPU 201.

The auxiliary storage device 204 is a computer-readable auxiliary storage that records various programs installed in the similar case image retrieval apparatus 120, and data generated by execution of the various programs. The characteristic quantity information DB 150 is implemented in the auxiliary storage device 204.

The coupling device 205 is coupled to the CT apparatus 110 and the image DB 130, and transmits and receives various types of data between the CT apparatus 110 and the image DB 130. The display device 206 displays a display screen used by a diagnostic radiologist or the like for performing comparative reading for a CT image of a diagnostic target, based on the control by the display control section 143. The operation device 207 receives various operations performed by a diagnostic radiologist on the similar case image retrieval apparatus 120.

The drive device 208 is a device for setting a recording medium 210. The recording medium 210 herein includes a medium that records information optically, electrically or magnetically, such as a CD-ROM, a flexible disk, or a magnetic optical disk. Alternatively, the recording medium 210 may include a semiconductor memory that records information electrically, such as a ROM, and a flash memory.

It is to be noted that the various programs stored in the auxiliary storage device 204 are installed, for instance, by setting distributed recording medium 210 to the drive device 208, and reading the various programs recorded on the recording medium 210 by the drive device 208. Alternatively, the various programs stored in the auxiliary storage device 204 may be downloaded from a network and installed via the coupling device 205.

Example Display of Display Screen

Next, the display screen displayed on the display device 206 by the display control section 143 will be described. FIGS. 3A and 3B and FIGS. 4A and 4B are first and second diagrams each illustrating an example display screen of the similar case image retrieval apparatus.

As illustrated in FIGS. 3A and 3B, the display screen 300 includes a diagnostic target image display area 310 for displaying a diagnostic target CT image captured by the CT apparatus 110.

In addition, the display screen 300 includes a retrieval condition specification area 320 for specifying a retrieval condition based on which a CT image of a disease case similar to the disease case of the diagnostic target CT image displayed on the diagnostic target image display area 310 is retrieved.

The retrieval condition specification area 320 is a specification area in which a diagnostic radiologist specifies that retrieval targets in the characteristic quantity information DB 150 are searched based on the distribution characteristic quantity calculated for predetermined types of abnormal shadows out of abnormal shadows extracted from the diagnostic target CT image.

It is to be noted that in the first embodiment, a shadow extracted from a CT image captured by the CT apparatus 110 is classified into one of five types of abnormal shadows and one type of normal shadow based on the image characteristic quantity. The five types of abnormal shadows include "consolidation", "ground-glass opacity", "honeycomb", "emphysema", and "nodule". When a diagnostic radiologist specifies at least one of the five types of abnormal shadows, the retrieval section 142 searches the retrieval targets in the characteristic quantity information DB 150 based on the distribution characteristic quantity calculated for the specified abnormal shadows.

Also, the display screen 300 includes a retrieval button 330. The retrieval button 330 is a button for instructing the retrieval section 142 to retrieve a target based on a retrieval condition.

Also, the display screen 300 includes a retrieval result display area 340. The retrieval result display area 340 displays results of search of the retrieval targets in the characteristic quantity information DB 150 based on the distribution characteristic quantity calculated for the diagnostic target CT image.

Also, the display screen 300 includes a similar case retrieval result display area 350. The similar case retrieval result display area 350 displays a CT image specified by a diagnostic radiologist out of retrieval results displayed on the retrieval result display area 340.

FIG. 3A illustrates the manner in which a diagnostic target CT image captured by the CT apparatus 110 is displayed on the diagnostic target image display area 310 of the display screen 300.

FIG. 3B illustrates the manner in which a retrieval condition is specified on the retrieval condition specification area 320 with a diagnostic target CT image displayed on the diagnostic target image display area 310 of the display screen 300. The example of FIG. 3B illustrates that "consolidation" and "ground-glass opacity" are specified as the retrieval condition.

Figure 4B:
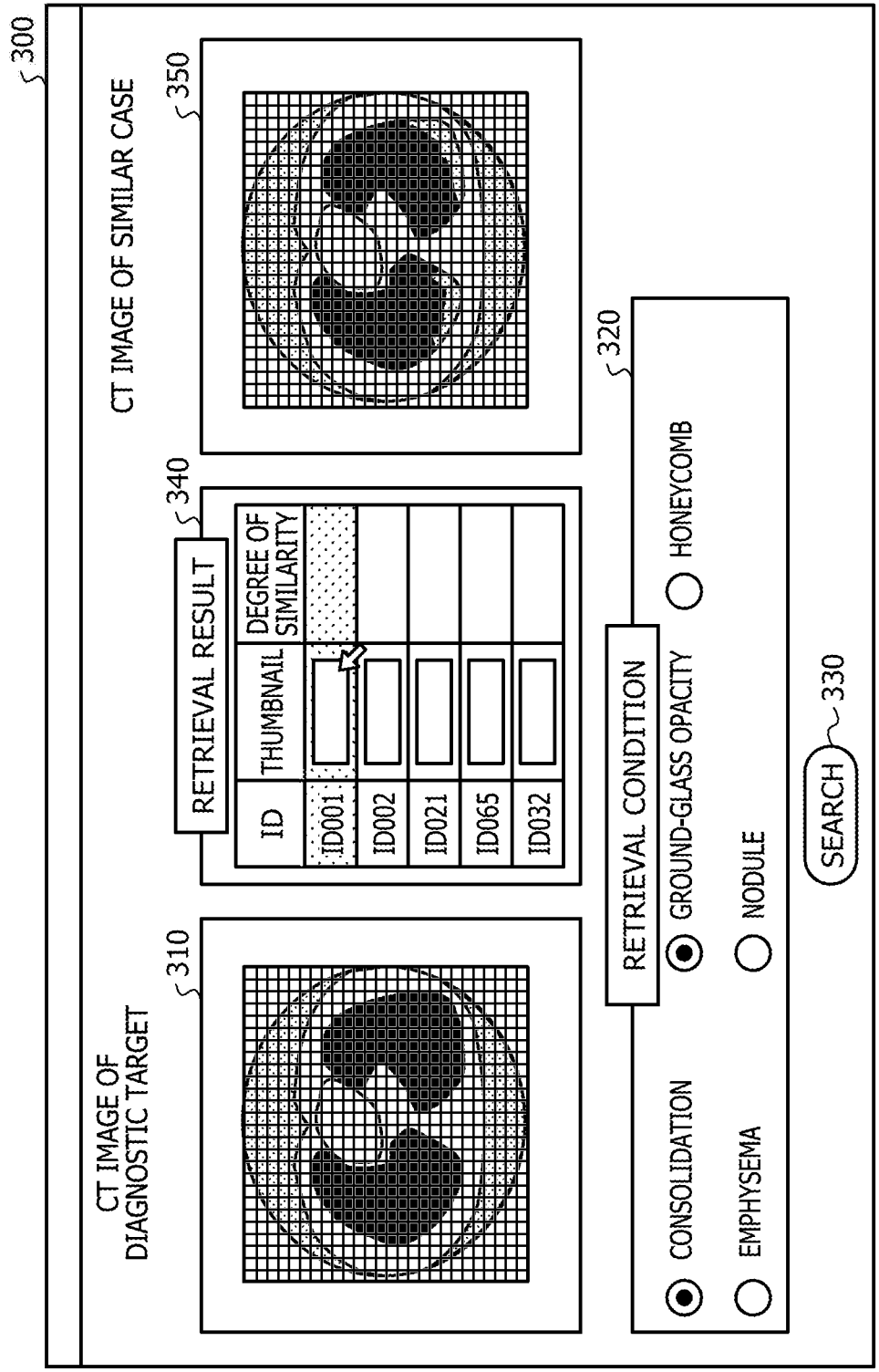

When the retrieval button 330 is pressed by a diagnostic radiologist in the state illustrated in FIG. 3B, transition is made to the display screen 300 illustrated in FIGS. 4A and 4B.

FIG. 4A illustrates the manner in which the identifiers of CT images are displayed on the retrieval result display area 340, the CT images being retrieval results obtained by the retrieval section 142 that has searched retrieval targets in the characteristic quantity information DB 150 triggered by pressing of the retrieval button 330.

As illustrated in FIG. 4A, the retrieval results displayed on the retrieval result display area 340 includes "ID", "thumbnail", and "degree of similarity" as information items. The "ID" stores the identifier for identifying each CT image retrieved by the retrieval section 142. In the "thumbnail", a thumbnail image of the CT image identified by the "ID" is displayed. The "degree of similarity" stores a degree of similarity of distribution characteristic quantity between the diagnostic target CT image and each CT image retrieved by the retrieval section 142. It is to be noted that the multiple retrieval results displayed on the retrieval result display area 340 are arranged in descending order of degree of similarity.

FIG. 4B illustrates the manner in which a predetermined retrieval result is selected by a diagnostic radiologist from the retrieval results displayed on the retrieval result display area 340, and a CT image corresponding to the selected retrieval result is displayed on the similar case retrieval result display area 350.

Specifically, the example of FIG. 4B illustrates the manner in which a retrieval result (ID="ID001") with the highest degree of similarity is selected, and a corresponding CT image (CT image of a similar disease case) is displayed on the similar case retrieval result display area 350. Thus, a diagnostic radiologist may perform comparative reading to make a diagnosis of the diagnostic target CT image while referring to a CT image of a disease case similar to the disease case of the diagnostic target CT image.

It is to be noted that the content of display on the display screen 300 is not limited to what is illustrated in FIGS. 3A and 3B and FIGS. 4A and 4B, and for instance, information on a diagnostic target patient may be displayed. Alternatively, a variety of information stored in the image DB 130 may be displayed in association with a CT image displayed on the similar case retrieval result display area 350.

Characteristic Quantity Information DB and Image DB

Next, the details of characteristic quantity information stored in the characteristic quantity information DB 150 and the CT image information stored in the image DB 130 will be described. FIG. 5 is a table illustrating example characteristic quantity information stored in the characteristic quantity information DB.

As illustrated in FIG. 5, characteristic quantity information 500 includes "ID", "thumbnail image", "type", "number of pieces", "distribution characteristic quantity" as information items.

The "ID" stores the identifier for identifying a CT image stored in the image DB 130. The "thumbnail" stores the file name of a thumbnail image of a CT image. The "type" stores information indicating the type of a shadow extracted from a CT image. As described above, in the first embodiment, a shadow extracted from a CT image is classified into one of the five types of abnormal shadows and one type of normal shadow. Thus, the "type" stores the five types of abnormal shadows (here, referred to as abnormal shadows 1 to 5 for the sake of convenience) and one type of normal shadow. The "number of pieces" stores the later-described number of blocks identified as each type of shadow in a CT image.

The "distribution characteristic quantity" stores the coordinates (x, y) of each shadow extracted from a CT image, where the number of the coordinates is the number stored in the "number of pieces". It is to be noted that the coordinates stored in the "distribution characteristic quantity" indicates the coordinates of each shadow in an image mapped having a predetermined shape from a CT image. The image having a predetermined shape is an image having a shape that may identify an abnormal shadow is distributed in which one of a first portion (central portion) in the lung regions (in the organ region), and a second portion (peripheral portion) that has an organizationally different occurrence portion from the first portion. It is to be noted that in the first embodiment, a description is given under the assumption that the image having a predetermined shape is a rectangular image.

FIG. 6 is a table illustrating example CT image information stored in the image DB. As illustrated in FIG. 6, CT image information 600 includes "ID", "image", "patient information", "diagnostic result", and "diagnostician" as information items.

The "ID" stores the identifier for identifying a CT image stored in the image DB 130. The "image" stores the file name of a CT image file. The "patient information" stores detailed information (such as the patient ID, name, age, sex) on a patient for whom a CT image is captured. The "diagnostic result" stores a diagnostic result for a CT image. The "diagnostician" stores a ID for identifying a diagnostic radiologist who makes a diagnosis of a corresponding CT image.

It is to be noted that diagnosis of a CT image stored in the image DB may be made at the time of capturing the CT image or at a predetermined timing after the capturing. Also, in addition to a diagnostic result, a variety of information such as the details of the treatment performed on the patient and the state after the treatment may be stored in association with the diagnostic result.

Functional Configuration of Registration Section of Similar Case Image Retrieval Apparatus Next, the details of the registration section 141 and the retrieval section 142 out of the sections (the registration section 141, the retrieval section 142, the display control section 143) of the similar case image retrieval apparatus 120 will be described sequentially. First, the details of the registration section 141 will be described.

Figure 7:
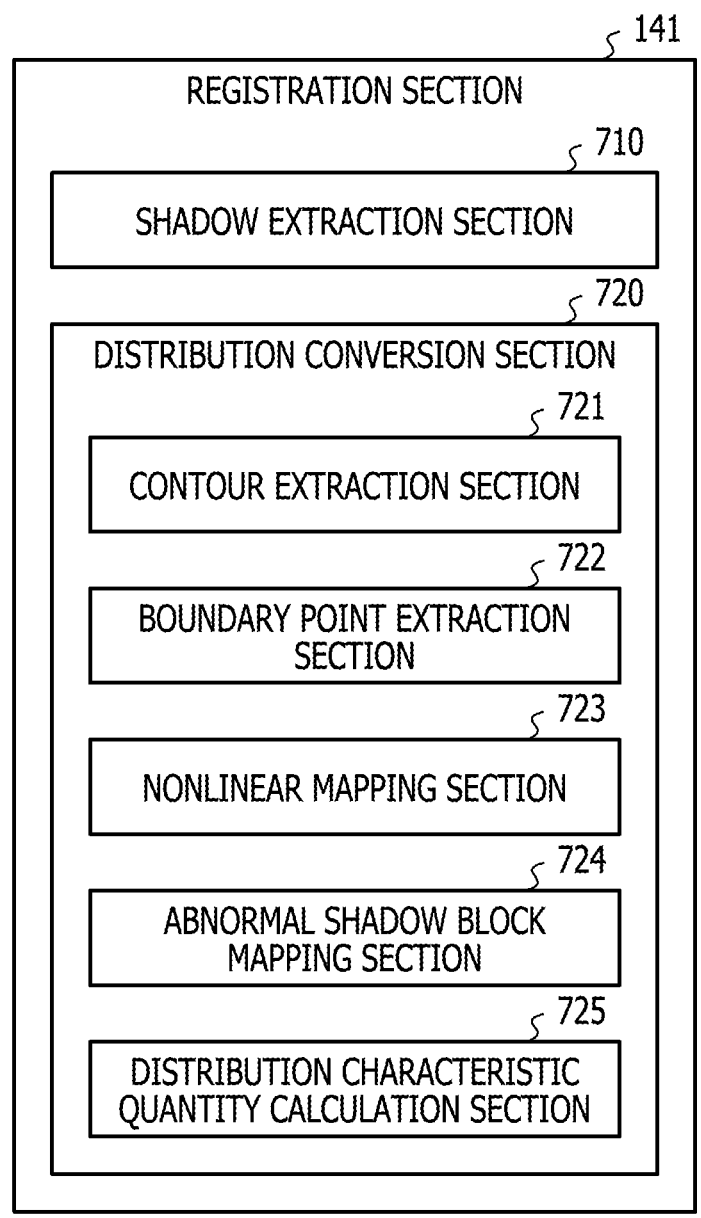
FIG. 7 is a diagram illustrating an example functional configuration of a registration section of the similar case image retrieval apparatus.

FIG. 7 is a diagram illustrating an example functional configuration of the registration section of the similar case image retrieval apparatus. As illustrated in FIG. 7, the registration section 141 has a shadow extraction section 710 and a distribution conversion section 720.

When a CT image of a patient is captured by the CT apparatus 110 after a diagnostic radiologist starts the registration section 141 to input information on the patient, the shadow extraction section 710 and the distribution conversion section 720 of the registration section 141 operate.

The shadow extraction section 710 obtains a CT image (for instance, the file name="IMAGE001") captured by the CT apparatus 110, and stores the CT image with an ID labeled along with the patient information in the image DB 130. In addition, the shadow extraction section 710 performs shadow extraction processing for extracting a shadow from the obtained CT image.

Specifically, the shadow extraction section 710 first divides the CT image into grids of a specified size, thereby generating partial images (hereinafter referred to as "blocks"). Also, as the image characteristic quantity, the shadow extraction section 710 extracts a multi-dimensional vector which is calculated by statistically processing the luminance value of each pixel included in each of the generated blocks. Furthermore, the shadow extraction section 710 identifies a shadow (consolidation, ground-glass opacity, honeycomb, emphysema, nodule, normal) corresponding to each block based on the extracted multi-dimension vector.

It is to be noted that for identifying a shadow corresponding to each block based on the extracted multi-dimension vector, it is assumed that the shadow extraction section 710 pre-calculates a representative vector indicating each shadow (consolidation, ground-glass opacity, honeycomb, emphysema, nodule, normal). The shadow extraction section 710 calculates the distance between the multi-dimension vector extracted from each block and a pre-calculated representative vector indicating each shadow, thereby identifying a shadow corresponding to a representative vector with the shortest distance.

The shadow extraction section 710 counts the number of blocks of the identified shadow, for each type of shadow, and stores the number of blocks along with the ID and thumbnail image of the CT image in the characteristic quantity information 500.

The distribution conversion section 720 has a contour extraction section 721, a boundary point extraction section 722, a nonlinear mapping section 723, an abnormal shadow block mapping section 724, and a distribution characteristic quantity calculation section 725. The distribution conversion section 720 maps each block in the CT image generated by the shadow extraction section 710 to a rectangular image by the operation of the sections 721 to 725 of the distribution conversion section 720, and calculates the coordinates of each block in the mapped image.

Specifically, the contour extraction section 721 performs contour extraction processing, and extracts the contour of the lung regions from the CT image. The contour extraction section 721 extracts a reduced contour (referred to as a first reduced contour) obtained by reducing the extracted contour. In addition, the contour extraction section 721 extracts a second reduced contour obtained by reducing the extracted first reduced contour. Similarly, contour extraction section 721 extracts nth reduced contour (n is an integer greater than or equal to 3).

The boundary point extraction section 722 performs boundary point extraction processing for extracting a boundary point to separate a central portion and a peripheral portion from the contour of each lung region extracted by the contour extraction section 721. The boundary point extraction section 722 extracts two points of boundary points indicating both ends of the central portion, and two points of boundary points indicating both ends of the peripheral portion from each of the lung regions on the right and left in the CT image.

The boundary point extraction section 722 performs the same processing on the first to nth reduced contours, and extracts two points of boundary points indicating both ends of a central portion, and two points of boundary points indicating both ends of a peripheral portion from each of the reduced contours.

The nonlinear mapping section 723 performs nonlinear mapping processing, and maps the contour of a central portion out of the contours of the lung regions extracted by the contour extraction section 721 so that the boundary points indicating both ends of the central portion correspond to two vertex positions on the contour of a rectangular image. The nonlinear mapping section 723 maps the contour of a peripheral portion out of the contours of the lung regions extracted by the contour extraction section 721 so that the boundary points indicating both ends of a peripheral portion correspond to the other two vertex positions on the contour of a rectangular image.

Furthermore, the nonlinear mapping section 723 also maps the first to nth reduced contours to the contour of a reduced rectangle by the same method. It is to be noted that the contour of a reduced rectangle is a contour obtained by reducing the contour of a rectangular image.

The abnormal shadow block mapping section 724 is an example of mapping section, and performs abnormal shadow block mapping processing, then maps each block to a rectangular image, the block being positioned between the contours of the lung regions to which mapping is performed by the nonlinear mapping section 723 and the first to nth reduced contours. The abnormal shadow block mapping section 724 maps each block to a rectangular image so that the positional relationship of each block with respect to the contours of the lung regions and the first to nth reduced contours is maintained before and after the mapping.

The distribution characteristic quantity calculation section 725 is an example of calculation section, and performs distribution characteristic quantity calculation processing, then calculates the position (x coordinate and y coordinate in a rectangular image) of a destination point to which each point is mapped by the abnormal shadow block mapping section 724, as the distribution characteristic quantity. The distribution characteristic quantity calculation section 725 stores the distribution characteristic quantity in the characteristic quantity information 500 in association with the ID of a CT image.

Figure 8A:
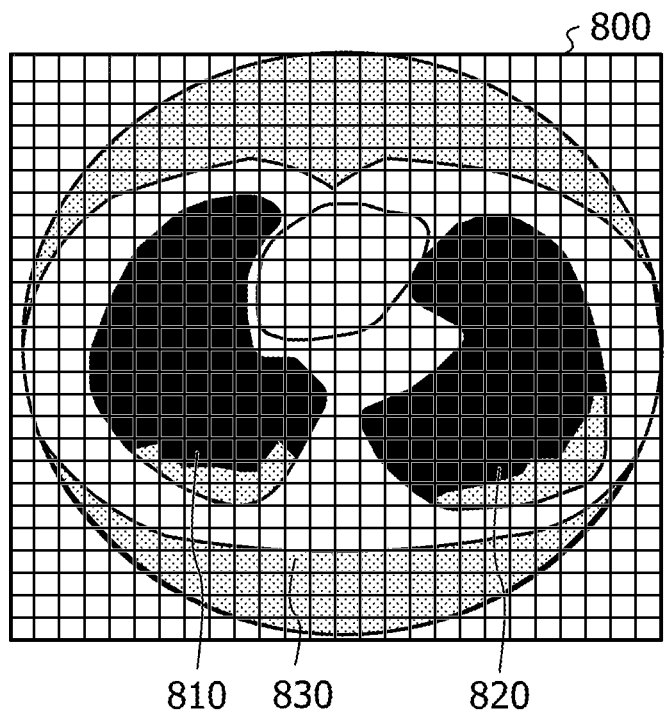
FIGS. 8A and 8B are each a diagram illustrating an example of shadow extraction processing performed by a shadow extraction section.
Figure 8B:
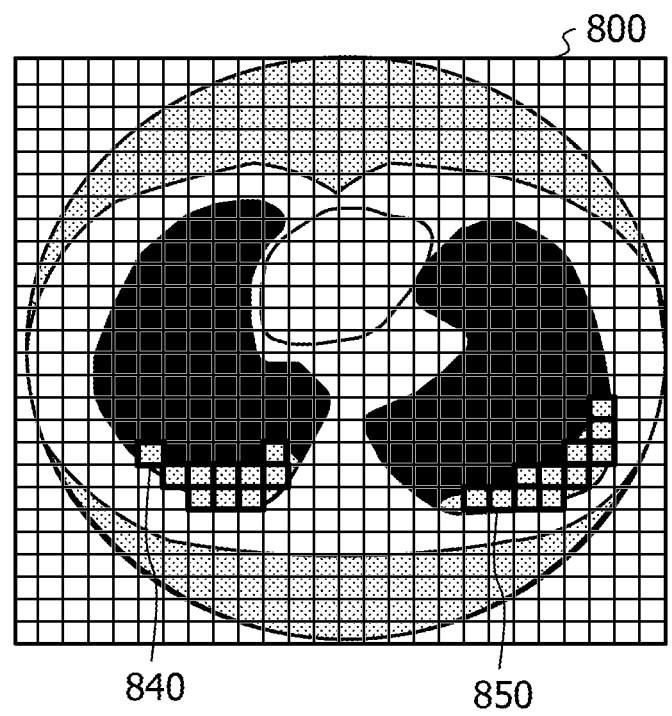

Specific Example of Processing of Registration Section of Similar Case Image Retrieval Apparatus Next, a specific example of processing performed by the registration section 141 of the similar case image retrieval apparatus 120 will be described. First, the shadow extraction processing performed by the shadow extraction section 710 of the registration section 141 will be described. FIGS. 8A and 8B are each a diagram illustrating a specific example of the shadow extraction processing performed by the shadow extraction section.

FIG. 8A illustrates an example CT image obtained by the shadow extraction section 710 from the CT apparatus 110. As illustrated in FIG. 8A, a CT image 800 includes a lung region 810 of the right lung of a patient, and a lung region 820 of the left lung of the patient. The grids (for instance, a grid 830) on the CT image 800 indicate the blocks generated by the shadow extraction section 710.

FIG. 8B illustrates the manner in which each block generated by the shadow extraction section 710 is identified as which shadow. The blocks (for instance, blocks 840, 850) illustrated by a thick line out of the blocks illustrated in FIG. 8B each indicate a block that is identified as abnormal shadow (for instance, consolidation). In contrast, blocks other than the blocks (for instance, blocks 840, 850) illustrated by a thick line each indicate a block that is identified as normal shadow.

Figure 9A:
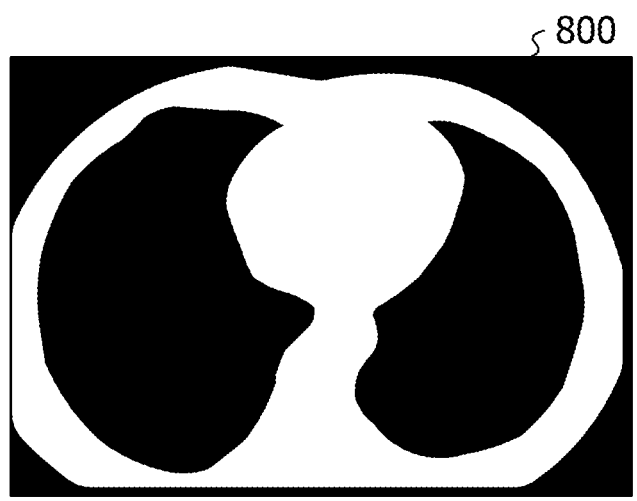
FIGS. 9A and 9B are each a diagram illustrating an example of contour extraction processing performed by a distribution conversion section.
Figure 9B:
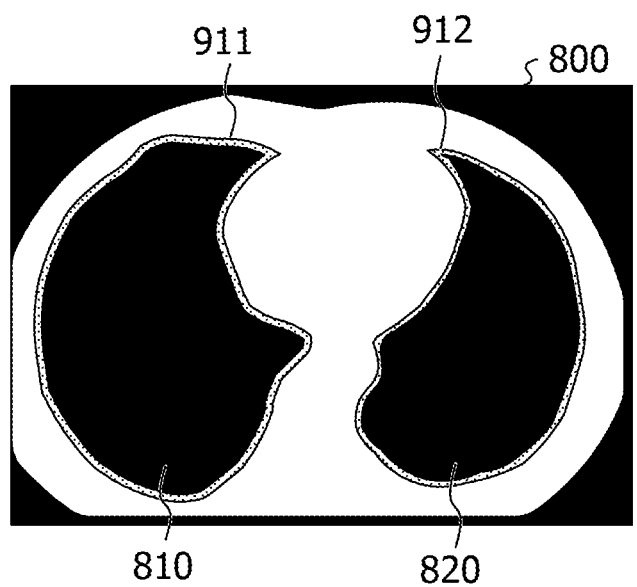

Next, the contour extraction processing performed by the contour extraction section 721 of the distribution conversion section 720 will be described. FIGS. 9A and 9B are each a diagram illustrating a specific example of the contour extraction processing performed by the distribution conversion section. FIG. 9A illustrates the CT image 800 before the contour extraction processing is performed by the contour extraction section 721 of the distribution conversion section 720. On the other hand, FIG. 9B illustrates the manner in which the contour extraction section 721 of the distribution conversion section 720 extracts lung regions 810, 820 from the CT image 800, and extracts contours 911, 912 of the lung regions 810, 820.

Next, the boundary point extraction processing performed by the boundary point extraction section 722 of the distribution conversion section 720 will be described. FIGS. 10A to 10F are each a diagram illustrating a specific example of the boundary point extraction processing performed by the distribution conversion section. The boundary point extraction section 722 of the distribution conversion section 720 calculates respective centroids of the lung regions 810, 820 on the right and left, and calculates a midpoint 1011 of the calculated centroids (see FIG. 10A).

Figure 10A:
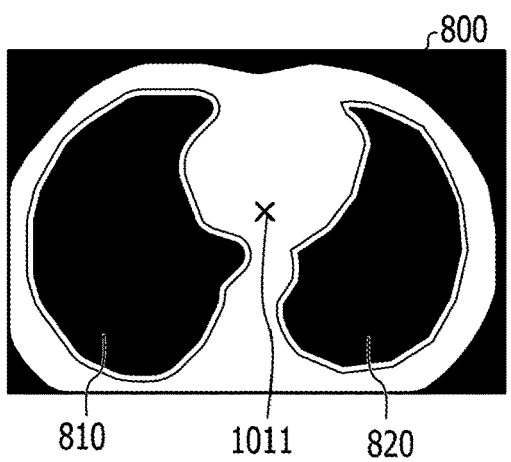
FIGS. 10A to 10F are each a diagram illustrating an example of boundary point extraction processing performed by the distribution conversion section.
Figure 10D:
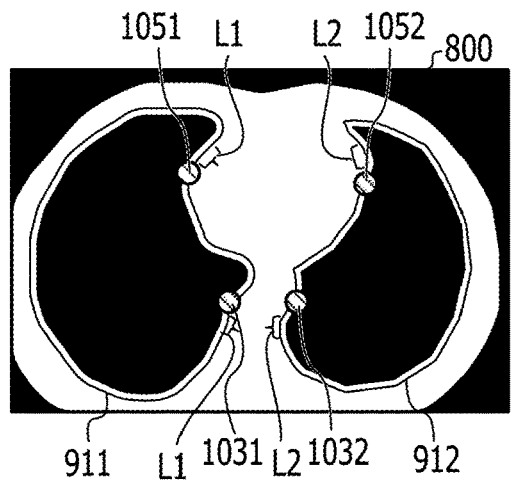
Figure 10B:
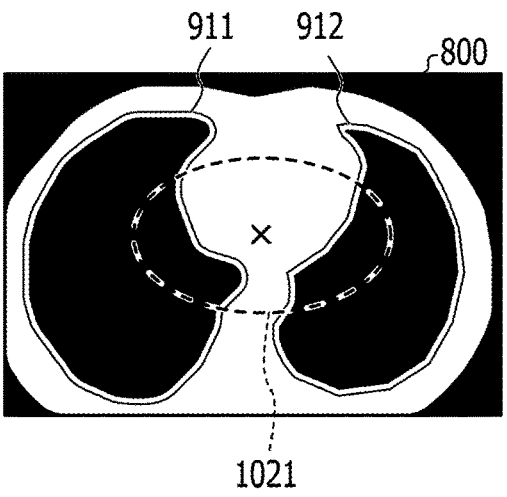

In addition, the boundary point extraction section 722 determines an ellipse 1021 of a predetermined size with the center at the midpoint 1011, and calculates intersection points of the ellipse 1021 and the contours 911, 912 of the lung regions 810, 820 (see FIG. 10B).

Figure 10E:
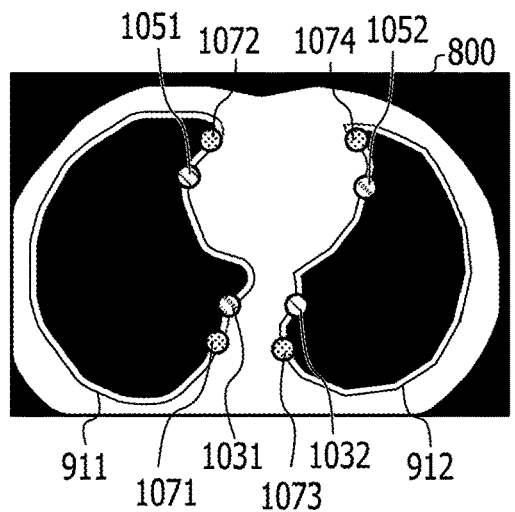
Figure 10C:
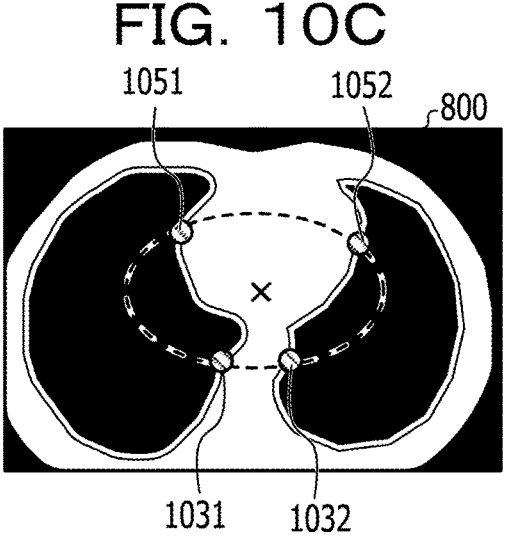
Figure 10F:
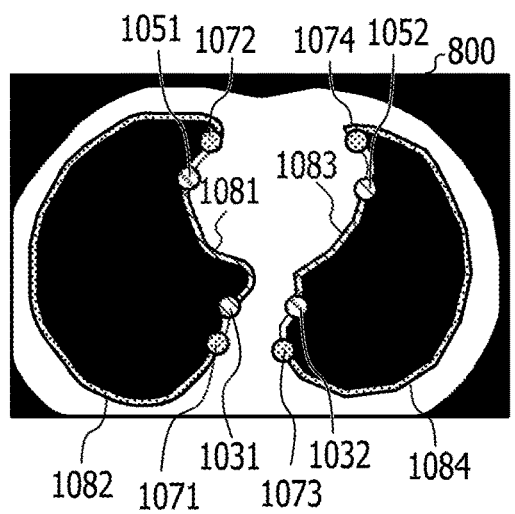

Also, the boundary point extraction section 722 extracts the intersection points of the ellipse 1021 and the contours 911, 912 as boundary points 1031, 1032, 1051, 1052 indicating both ends of a central portion (see FIG. 10C).

Also, the boundary point extraction section 722 calculates a length L1 by multiplying the total length of the contour 911 by a predetermined coefficient (α), and identifies the position which is on the contour 911 and the length L1 away from the boundary point 1051 in a counterclockwise direction. The boundary point extraction section 722 also identifies the position which is on the contour 911 and the length L1 away from the boundary point 1031 in a clockwise direction (FIG. 10D).

Similarly, the boundary point extraction section 722 calculates a length L2 by multiplying the total length of the contour 912 by a predetermined coefficient (α), and identifies the position which is on the contour 912 and the length L2 away from the boundary point 1052 in a clockwise direction. The boundary point extraction section 722 also identifies the position which is on the contour 912 and the length L2 away from the boundary point 1032 in a counterclockwise direction (FIG. 10D).

Also, the boundary point extraction section 722 extracts a boundary point 1071 the length L1 away from the boundary point 1031 in a clockwise direction, and a boundary point 1072 the length L1 away from the boundary point 1051 in a counterclockwise direction (FIG. 10E). Also, the boundary point extraction section 722 extracts a boundary point 1073 the length L2 away from the boundary point 1032 in a counterclockwise direction, and a boundary point 1074 the length L2 away from the boundary point 1052 in a clockwise direction (FIG. 10E).

Furthermore, from the contour 911, the boundary point extraction section 722 extracts a contour 1081 having both ends at the boundary point 1031 and the boundary point 1051 as the contour of the central portion of the right lung. Also, from the contour 911, the boundary point extraction section 722 extracts a contour 1082 having both ends at the boundary point 1071 and the boundary point 1072 as the contour of the peripheral portion of the right lung.

Also, from the contour 912, the boundary point extraction section 722 extracts a contour 1083 having both ends at the boundary point 1032 and the boundary point 1052 as the contour of the central portion of the left lung. Also, from the contour 912, the boundary point extraction section 722 extracts a contour 1084 having both ends at the boundary point 1073 and the boundary point 1074 as the contour of the peripheral portion of the left lung.

Figure 11A:
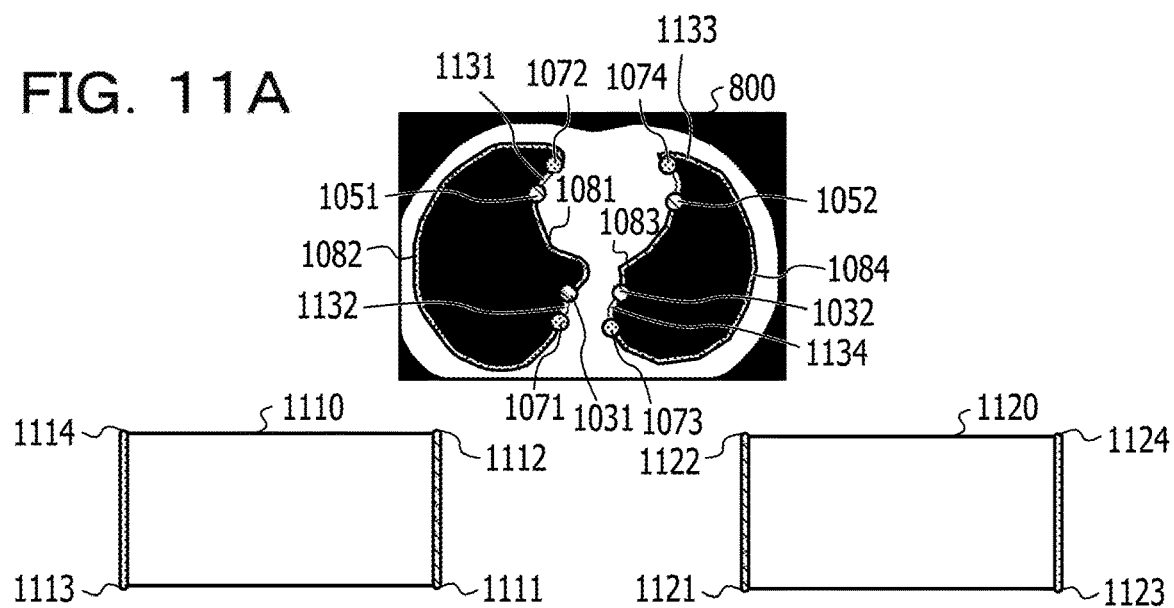
FIGS. 11A to 11C are each a diagram illustrating an example of nonlinear mapping processing performed by the distribution conversion section.
Figure 11B:
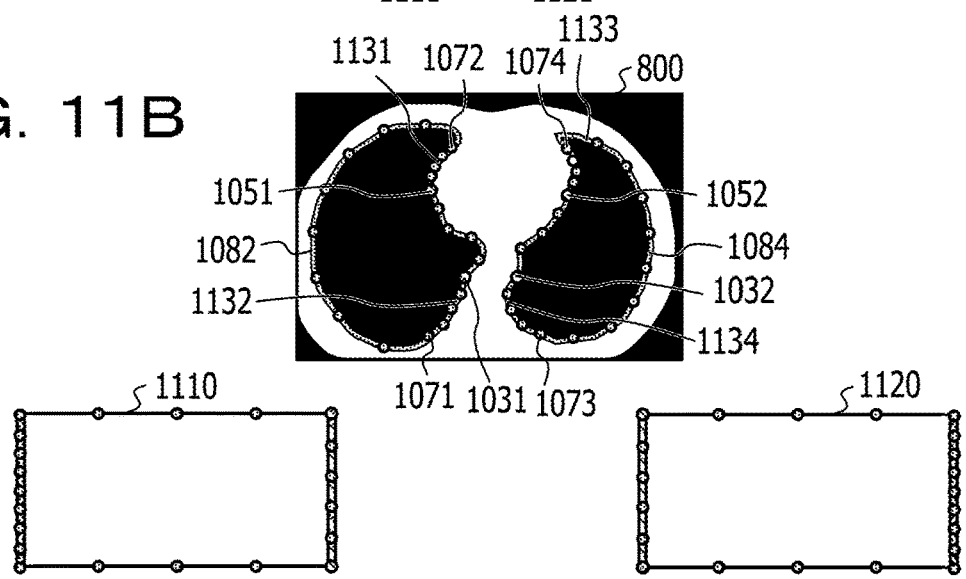
Figure 11C:
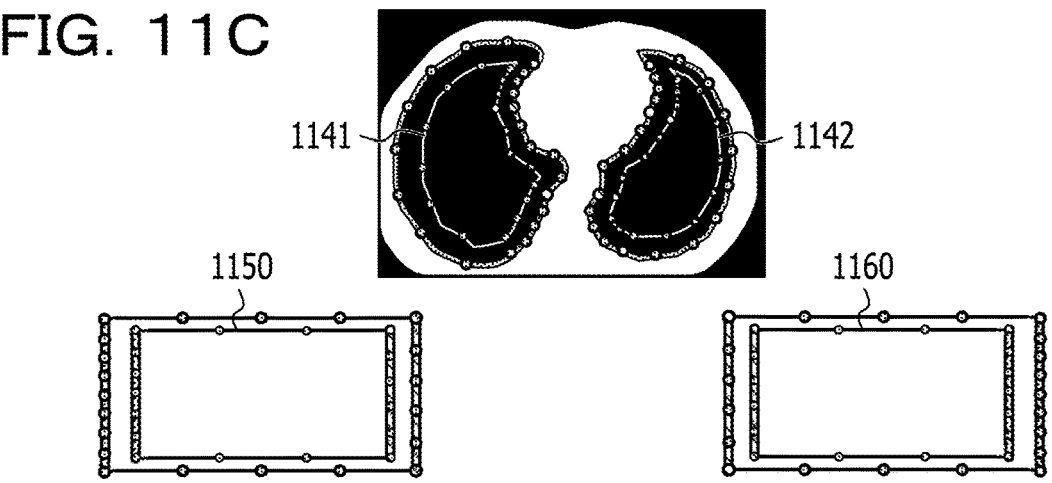

Next, the nonlinear mapping processing performed by the nonlinear mapping section 723 of the distribution conversion section 720 will be described. FIGS. 11A to 11C are each a diagram illustrating a specific example of the nonlinear mapping processing performed by the distribution conversion section. As illustrated in FIG. 11A, the nonlinear mapping section 723 of the distribution conversion section 720 maps the contour 1081 extracted by the boundary point extraction section 722 to a fixed contour which is part of the contour of a rectangular image 1110. Specifically, the contour 1081 is mapped so that the boundary points 1031, 1051 indicating both ends of the central portion correspond to two vertices 1111, 1112 of the contour of the rectangular image 1110.

Also, the nonlinear mapping section 723 maps the contour 1082 extracted by the boundary point extraction section 722 to other fixed contour which is part of the contour of the rectangular image 1110. Specifically, the contour 1082 is mapped so that the boundary points 1071, 1072 indicating both ends of the peripheral portion correspond to two vertices 1113, 1114 of the contour of the rectangular image 1110.

It is to be noted that for the mapping, the nonlinear mapping section 723 extracts sample points at regular intervals from the contours 1081, 1082, and performs mapping so that mapped sample points are arranged at regular intervals (see circle marks of FIG. 11B).

As illustrated in FIG. 11A, the nonlinear mapping section 723 maps the contour 1083 extracted by the boundary point extraction section 722 to a fixed contour which is part of the contour of a rectangular image 1120. Specifically, the contour 1083 is mapped so that the boundary points 1032, 1052 indicating both ends of the central portion correspond to two vertices 1121, 1122 of the contour of the rectangular image 1120.

Also, the nonlinear mapping section 723 maps the contour 1084 extracted by the boundary point extraction section 722 to other fixed contour which is part of the contour of the rectangular image 1120. Specifically, the contour 1084 is mapped so that the boundary points 1073, 1074 indicating both ends of the peripheral portion correspond to two vertices 1123, 1124 of the contour of the rectangular image 1120.

It is to be noted that for the mapping, the nonlinear mapping section 723 extracts sample points at regular intervals from the contours 1083, 1084, and performs mapping so that mapped sample points are arranged at regular intervals (see circle marks of FIG. 11B).

As illustrated in FIG. 11A, the nonlinear mapping section 723 maps a contour 1131 between the boundary point 1051 and the boundary point 1072 to a fixed contour which is part of the contour of the rectangular image 1110. Specifically, the contour 1131 is mapped so that the boundary point 1051 and the boundary point 1072 correspond to the two vertices 1112, 1114 of the contour of the rectangular image 1110.

Also, the nonlinear mapping section 723 maps a contour 1132 between the boundary point 1031 and the boundary point 1071 to other fixed contour which is part of the contour of the rectangular image 1110. Specifically, the contour 1132 is mapped so that the boundary point 1031 and the boundary point 1071 correspond to the two vertices 1111, 1113 of the contour of the rectangular image 1110.

It is to be noted that for the mapping, the nonlinear mapping section 723 extracts sample points at regular intervals from the contours 1131, 1132, and performs mapping so that mapped sample points are arranged at regular intervals (see circle marks of FIG. 11B).

Similarly, the nonlinear mapping section 723 maps a contour 1133 between the boundary point 1052 and the boundary point 1074 to a fixed contour which is part of the contour of the rectangular image 1120. Specifically, the contour 1133 is mapped so that the boundary point 1052 and the boundary point 1074 correspond to the two vertices 1122, 1124 of the contour of the rectangular image 1120.

Also, the nonlinear mapping section 723 maps a contour 1134 between the boundary point 1032 and the boundary point 1073 to other fixed contour which is part of the contour of the rectangular image 1120. Specifically, the contour 1134 is mapped so that the boundary point 1032 and the boundary point 1073 correspond to the two vertices 1121, 1123 of the contour of the rectangular image 1120.

It is to be noted that for the mapping, the nonlinear mapping section 723 extracts sample points at regular intervals from the contours 1133, 1134, and performs mapping so that mapped sample points are arranged at regular intervals (see circle marks of FIG. 11B).

As illustrated in FIG. 11C, the nonlinear mapping section 723 performs the same processing as described above on a first reduced contour 1141 of the right lung and a first reduced contour 1142 of the left lung, and performs mapping to a reduced fixed contour which is part of the contour of reduced rectangles 1150, 1160. Here, in the right lung, points corresponding to the boundary points 1031, 1051, 1071, 1072 are determined on the reduced contour 1141, the points being closest to the respective boundary points. Also, in the left lung, points corresponding to the boundary points determined similarly. It is to be noted that for the mapping, the nonlinear mapping section 723 extracts sample points at regular intervals from the first reduced contour 1141 of the right lung and the first reduced contour 1142 of the left lung. The nonlinear mapping section 723 performs mapping so that the sample points are at regular intervals in the reduced fixed contour which is part of the contour of the reduced rectangles 1150, 1160.

Furthermore, the nonlinear mapping section 723 performs the same processing on the second to nth reduced contours of the right lung and the second to nth reduced contours of the left lung, and performs mapping to reduced fixed contours which are respective parts of the contours of the second to nth reduced rectangles of the right lung and the second to nth reduced rectangles of the left lung. It is to be noted that for the mapping, the nonlinear mapping section 723 extracts sample points at regular intervals from the second to nth reduced contours of the right lung and the second to nth reduced contours of the left lung. The nonlinear mapping section 723 performs mapping so that the sample points are at regular intervals in each of the reduced fixed contours which are respective parts of the contours of the second to nth reduced rectangles.

Figure 12A:
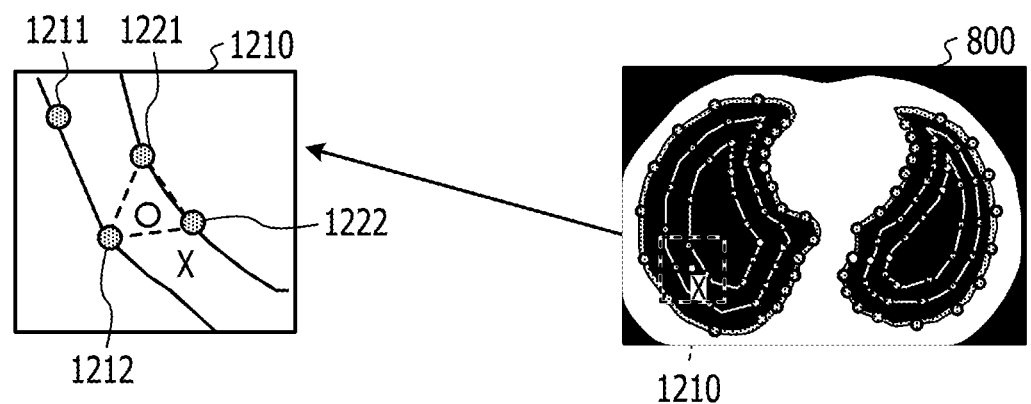
FIGS. 12A and 12B are each a diagram illustrating an example of abnormal shadow block mapping processing performed by the distribution conversion section.
Figure 12B:
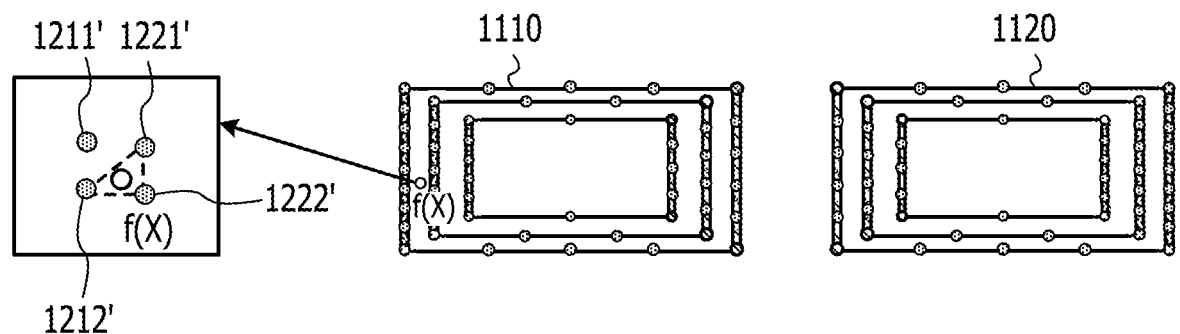

Next, the abnormal shadow block mapping processing performed by the abnormal shadow block mapping section 724 of the distribution conversion section 720 will be described. FIGS. 12A and 12B are each a diagram illustrating a specific example of the abnormal shadow block mapping processing performed by the distribution conversion section. As described above, the abnormal shadow block mapping section 724 of the distribution conversion section 720 maps each block to the rectangular images 1110, 1120, the block being positioned between the contours of the rectangular images 1110, 1120 and the first to nth reduced contours to which mapping is performed by the nonlinear mapping section 723. The abnormal shadow block mapping section 724 maps each block to the rectangular images 1110, 1120 so that the positional relationship of each block with respect to the contours of the rectangular images 1110, 1120 and the first to nth reduced contours is maintained before and after the mapping.

A specific description is given using FIGS. 12A and 12B. A symbol 1210 of FIG. 12A indicates an enlarged image of a portion of the CT image 800, sample points 1211, 1212 are on the first reduced contour of the right lung, and sample points 1221, 1222 are on the second reduced contour of the right lung. A block X is at a position surrounded by the sample points 1211, 1212, 1221, 1222.

When mapping the block X, the abnormal shadow block mapping section 724 extracts three points in a short distance (the sample points 1212, 1221, 1222) from the sample points 1211 to 1222 surrounding the block X (see FIG. 12A). Also, the abnormal shadow block mapping section 724 identifies the position on the rectangular image 1110 of each of sample points 1212', 1221', 1222' at mapping destinations to which mapping is performed by the nonlinear mapping section 723 (see FIG. 12B). It is to be noted that a symbol 1210' of FIG. 12B indicates an enlarged image of a portion of the rectangular image 1110.

Furthermore, the abnormal shadow block mapping section 724 calculates a relative position of the block X with respect to the three sample points 1212, 1221, 1222. The abnormal shadow block mapping section 724 maps the block X to the rectangular image 1110 so that the calculated relative position is maintained (see FIG. 12B).

The abnormal shadow block mapping section 724 maps all the blocks in the lung regions 810, 820 to the rectangular images 1110, 1120 by the same method.

Next, the distribution characteristic quantity calculation processing performed by the distribution characteristic quantity calculation section 725 of the distribution conversion section 720 will be described. FIG. 13 is a diagram illustrating a specific example of the distribution characteristic quantity calculation processing performed by the distribution conversion section. After the abnormal shadow block mapping section 724 maps all the blocks in the lung regions 810, 820 to the rectangular images 1110, 1120, the distribution characteristic quantity calculation section 725 calculates the coordinates of an abnormal shadow on the rectangular images 1110, 1120.

In FIG. 13, the blocks 840, 850 and other blocks on the rectangular images 1110, 1120 indicate the positions of the blocks 840, 850 and other blocks of an abnormal shadow after the mapping, extracted from the CT image 800 by the abnormal shadow block mapping section 724. The distribution characteristic quantity calculation section 725 calculates the coordinates of the blocks 840, 850 and other blocks of each abnormal shadow on the rectangular images 1110, 1120, and stores the coordinates as distribution characteristic quantity in the characteristic quantity information 500.

Functional Configuration of Retrieval Section of Similar Case Image Retrieval Apparatus Next, the details of the retrieval section 142 out of the sections (the registration section 141, the retrieval section 142, the display control section 143) of the similar case image retrieval apparatus 120 will be described.

Figure 14:
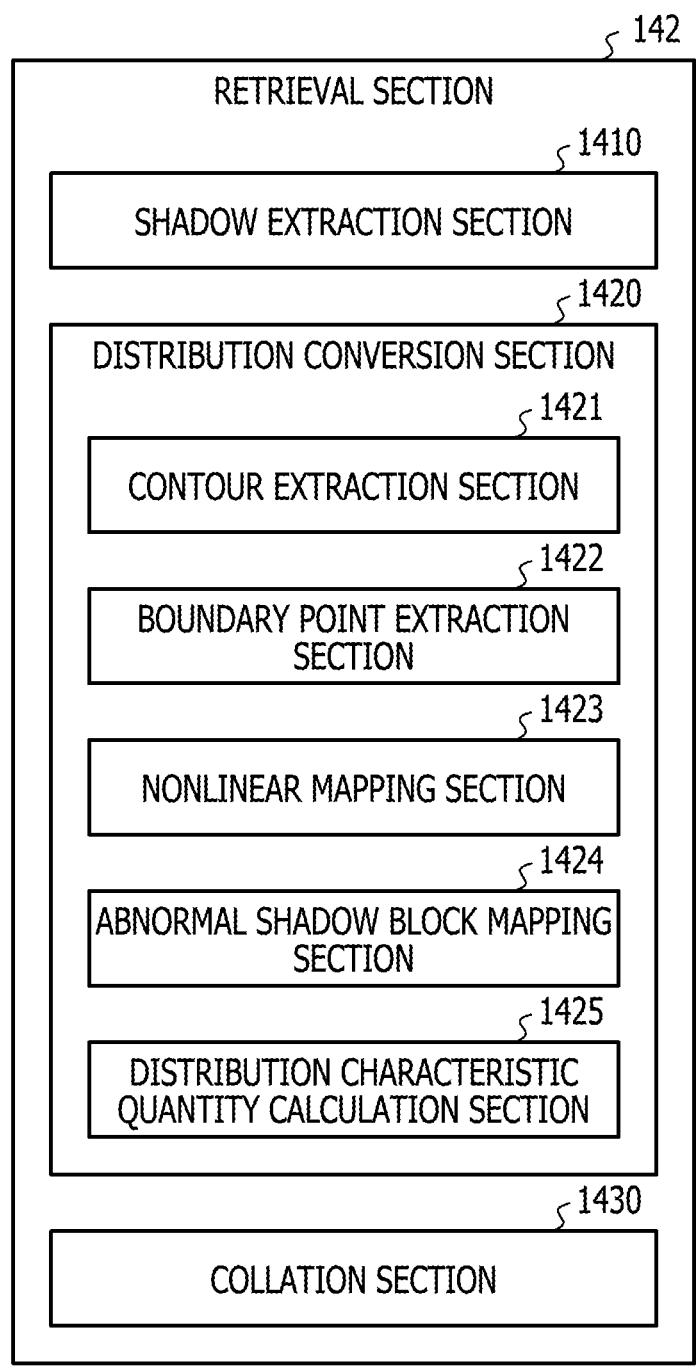
FIG. 14 is a diagram illustrating an example functional configuration of a retrieval section of the similar case image retrieval apparatus.

FIG. 14 is a diagram illustrating an example functional configuration of the retrieval section of the similar case image retrieval apparatus. As illustrated in FIG. 14, the retrieval section 142 has a shadow extraction section 1410, a distribution conversion section 1420, and a collation section 1430.

When a CT image of a patient is captured by the CT apparatus 110 after a diagnostic radiologist starts the retrieval section 142 to input information on the patient, the display control section 143 displays the captured CT image on the display screen 300 as a diagnostic target CT image. The display screen 300 is displayed by the display control section 143, input of various instructions by a diagnostic radiologist causes the shadow extraction section 1410, the distribution conversion section 1420, and the collation section 1430 of the retrieval section 142 to operate.

In addition to the processing on a diagnostic target CT image, the shadow extraction section 1410 and the distribution conversion section 1420 performs the same processing as that performed by the shadow extraction section 710 and the distribution conversion section 720 of the registration section 141 illustrated in FIG. 7, thus a description is omitted here.

The collation section 1430 performs collation processing, and calculates a total degree of similarity between the distribution characteristic quantity of abnormal shadows calculated based on a diagnostic target CT image, and the retrieval targets (the distribution characteristic quantities of abnormal shadows included in the CT images stored in the image DB 130) in the characteristic quantity information DB 150. The collation section 1430 calculates a total value (total degree of similarity) by adding the degree of similarity calculated for the right lung and the degree of similarity calculated for the left lung. Also, when multiple types of abnormal shadows are present, the collation section 1430 calculates a degree of similarity for each of the multiple types of abnormal shadows, and calculates a total value (total degree of similarity) by adding the degree of similarity calculated for each type of abnormal shadow. However, when a specific type of abnormal shadow is specified as the retrieval condition, a degree of similarity calculated for the specified type of abnormal shadow is a total degree of similarity. In the first embodiment, the collation section 1430 calculates a degree of similarity of between distribution characteristic quantities using, for instance, Earth Mover's Distance.

Also, the collation section 1430 performs sorting processing, and sorts the respective IDs associated with the retrieval targets in the characteristic quantity information DB 150 in descending order of total degree of similarity. Thus, a distribution characteristic quantity similar to the distribution characteristic quantity calculated for a diagnostic target CT image is retrieved. Furthermore, the collation section 1430 notifies the display control section 143 of IDs associated with retrieval targets having a high total degree of similarity as retrieval results.

Figure 15:
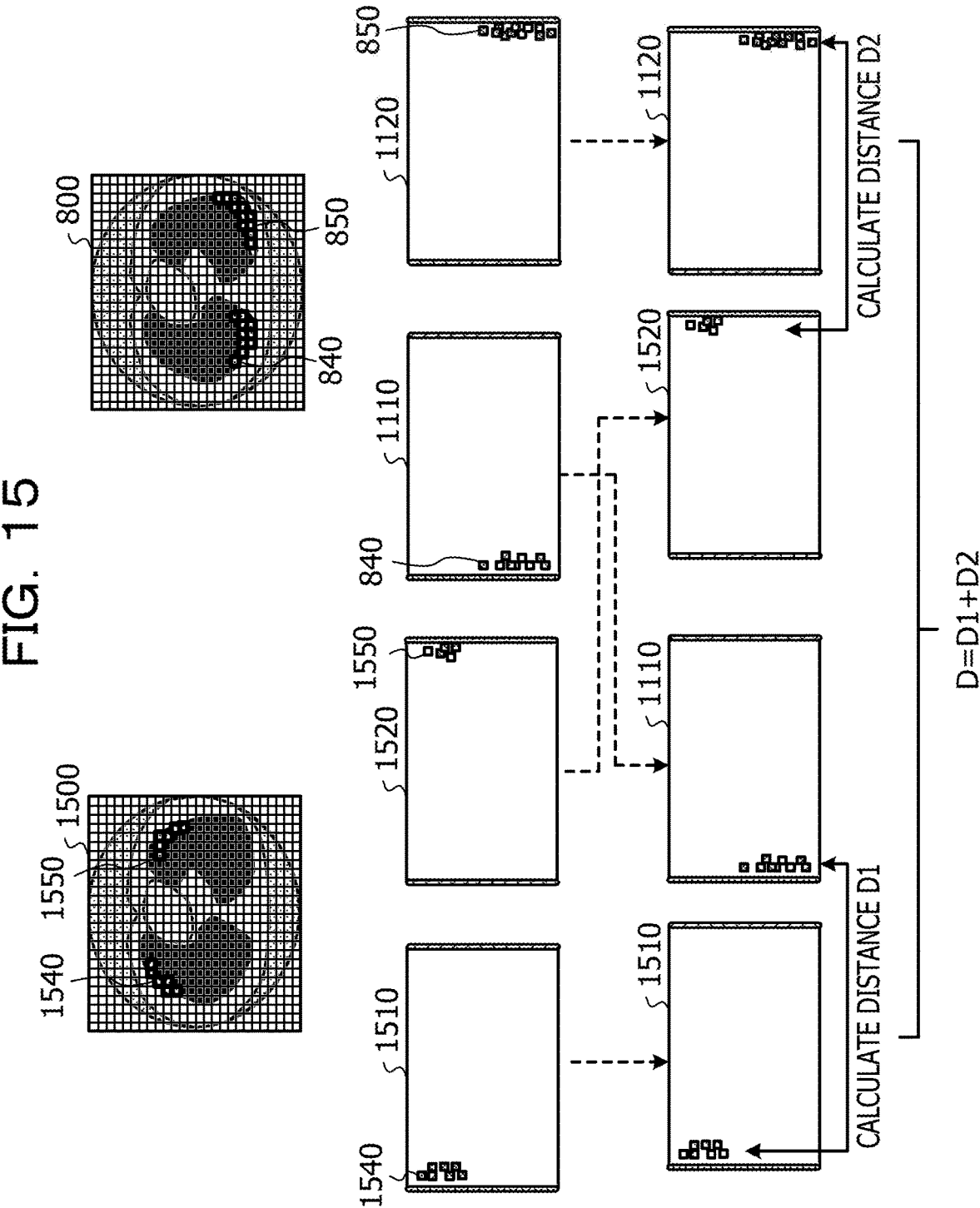
FIG. 15 is a diagram illustrating an example of collation processing performed by a collation section.

Specific Example of Processing of Retrieval Section of Similar Case Image Retrieval Apparatus Next, a specific example of collation processing performed by the collation section 1430 out of the processing performed by the retrieval section 142 of the similar case image retrieval apparatus 120 will be described. FIG. 15 is a diagram illustrating a specific example of the collation processing performed by the collation section.

In FIG. 15, a CT image 1500 is an example of diagnostic target CT image obtained from the CT apparatus 110 by the shadow extraction section 1410. Also, the rectangular images 1510, 1520 indicate the state after the blocks of abnormal shadow extracted from the diagnostic target CT image 1500 are mapped by the distribution conversion section 1420. The distribution conversion section 1420 calculates the coordinates of each block (for instance, the blocks 1540, 1550) of abnormal shadow in the rectangular images 1510, 1520 as the distribution characteristic quantity.

In contrast, the CT image 800 is a CT image in which a distribution characteristic quantity is included by the registration section 141, and is a target CT image for which a total degree of similarity to the CT image 1500 is calculated by the collation section 1430. Although the collation section 1430 calculates a degree of similarity by reading a distribution characteristic quantity from the characteristic quantity information DB 150, in order to simplify a description, the CT image 800 corresponding to the read distribution characteristic quantity is illustrated.

In FIG. 15, the rectangular images 1110, 1120 indicate the state after the blocks of abnormal shadow extracted from the CT image 800 are mapped by the distribution conversion section 720. The collation section 1430 reads the coordinates of each block (for instance, the blocks 840, 850) of abnormal shadow in the rectangular images 1110, 1120 as the distribution characteristic quantity from the characteristic quantity information DB 150.

As illustrated in FIG. 15, the collation section 1430 calculates a degree of similarity between the distribution characteristic quantity calculated from the rectangular image 1510 of the right lung out of the diagnostic target CT image 1500, and the distribution characteristic quantity calculated from the rectangular image 1110 of the right lung out of the CT image 800. Specifically, the distance D1 between each block of abnormal shadow (for instance, the block 1540) in the rectangular image 1510, and each block of abnormal shadow (for instance, the block 840) in the rectangular image 1110 is calculated by Earth Mover's Distance.

Also, the collation section 1430 calculates a degree of similarity between the distribution characteristic quantity calculated from the rectangular image 1520 of the left lung out of the diagnostic target CT image 1500, and the distribution characteristic quantity calculated from the rectangular image 1120 of the left lung out of the CT image 800. Specifically, the distance D2 between each block (for instance, the block 1550) of abnormal shadow in the rectangular image 1520, and each block (for instance, the block 850) of abnormal shadow in the rectangular image 1120 is calculated by Earth Mover's Distance.

Furthermore, the collation section 1430 calculates a total degree of similarity by adding a degree of similarity calculated for each lung together. Specifically, the collation section 1430 calculates D=D1+D2 as the total degree of similarity.

Similar Case Image Retrieval Processing in CT Image Processing System

Figure 16:
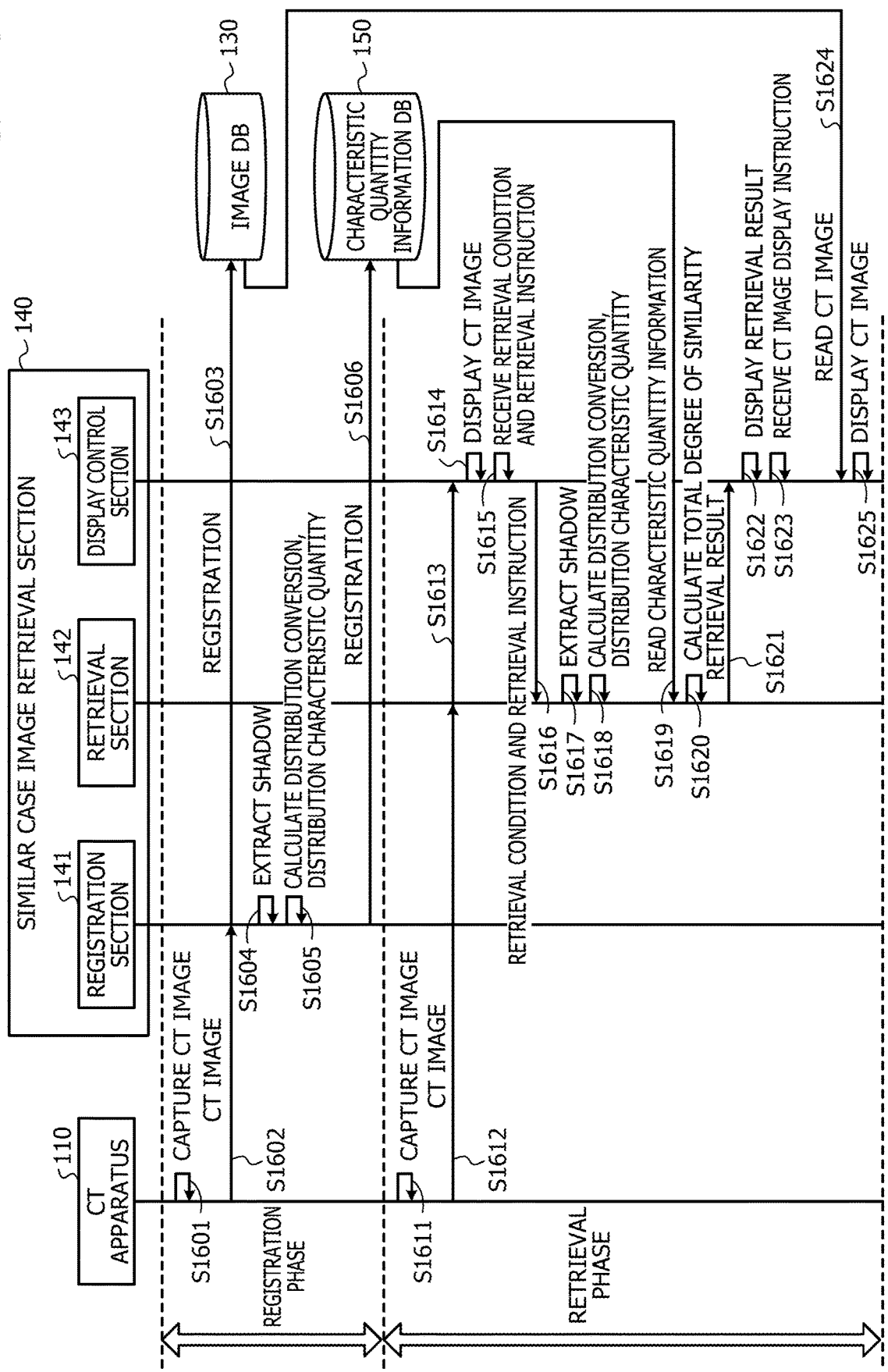
FIG. 16 is a sequence diagram of similar case image retrieval processing in a CT image processing system.

Next, the flow of the entire similar case image retrieval processing in the CT image processing system 100 will be described. FIG. 16 is a sequence diagram of the similar case image retrieval processing in the CT image processing system.

As illustrated in FIG. 16, the similar case image retrieval processing may be roughly divided into a registration phase and a retrieval phase. First, the registration phase will be described.

In step S1601, the CT apparatus 110 captures a CT image 800 of a patient. When the CT image 800 is captured, patient information is inputted to the similar case image retrieval apparatus 120.

In step S1602, the CT apparatus 110 transmits the CT image 800 obtained by the capturing to the registration section 141 of the similar case image retrieval apparatus 120.

In step S1603, the registration section 141 obtains the CT image 800 transmitted from the CT apparatus 110, and the CT image with an identifier assigned along with the patient information in the image DB 130. It is to be noted that when the CT image 800 is stored in the image DB 130 by the registration section 141, a diagnostic radiologist may make a diagnosis of the CT image 800, and a diagnostic result may be stored as well.

In step S1604, the registration section 141 divides the obtained CT image 800 into multiple blocks, and identifies the type of shadow for each block.

In step S1605, the registration section 141 calculates a distribution characteristic quantity by mapping each block with the identified type of shadow to the rectangular images 1110, 1120.

In step S1606, the registration section 141 stores the calculated distribution characteristic quantity in the characteristic quantity information DB 150 for each identified type of shadow in association with the identifier of the CT image 800.

The registration phase is completed now. It is to be noted that FIG. 16 is an example of processing for one patient in the registration phase, and practically, processing for multiple patients is performed in the registration phase.

Next, the retrieval phase will be described. In step S1611, the CT apparatus 110 captures a CT image 1500 of a diagnostic target patient. When the CT image 1500 is captured, patient information on a diagnostic target patient is inputted to the similar case image retrieval apparatus 120.

In step S1612, the CT apparatus 110 transmits the CT image 1500 obtained by the capturing to the retrieval section 142 of the similar case image retrieval apparatus 120.

In step S1613, the retrieval section 142 obtains the CT image 1500 transmitted from the CT apparatus 110. Also, the retrieval section 142 notifies the display control section 143 of the obtained CT image 1500.

In step S1614, the display control section 143 displays the display screen 300, and displays the CT image 1500 notified from the retrieval section 142 on the diagnostic target image display area 310 of the display screen 300.

In step S1615, the display control section 143 receives the retrieval condition specified in the retrieval condition specification area 320 of the display screen 300. In addition, the display control section 143 receives an inputted retrieval instruction via the retrieval button 330.

In step S1616, the display control section 143 notifies the retrieval section 142 of the received retrieval condition and retrieval instruction.

In step S1617, upon receiving the retrieval instruction from the display control section 143, the retrieval section 142 divides the obtained CT image 1500 into multiple blocks, and identifies the blocks (for instance, the blocks 1540, 1550) of the type of abnormal shadow according to the retrieval condition.

In step S1618, the retrieval section 142 calculates a distribution characteristic quantity of the blocks (for instance, the blocks 1540, 1550) of the type of abnormal shadow according to the retrieval condition by mapping each block in the CT image 1500 to the rectangular images 1510, 1520.

In step S1619, the retrieval section 142 reads the characteristic quantity information 500 from the characteristic quantity information DB 150.

In step S1620, the retrieval section 142 calculates a total degree of similarity between the distribution characteristic quantity of each retrieval target included in the read characteristic quantity information 500, and the distribution characteristic quantity, calculated in step S1618, of the diagnostic target CT image 1500. In addition, the retrieval section 142 sorts the respective IDs associated with the retrieval targets in the characteristic quantity information 500 in descending order of calculated total degree of similarity.

In step S1621, the retrieval section 142 notifies the display control section 143 of respective IDs associated with a predetermined number of retrieval targets having a high total degree of similarity, and corresponding total degree of similarities, as retrieval results.

In step S1622, the display control section 143 displays the retrieval results notified from the retrieval section 142 on the retrieval result display area 340.

In step S1623, when a predetermined retrieval result is selected by a diagnostic radiologist in the retrieval result display area 340, the display control section 143 receives the selection as a CT image display instruction.

In step S1624, the display control section 143 identifies the ID included in the selected retrieval result, and reads the CT image 800 identified by the identified ID from the image DB 130.

In step S1625, the display control section 143 displays the read CT image 800 on the similar case retrieval result display area 350. Thus, a diagnostic radiologist may make a diagnosis of the diagnostic target CT image 1500 while referring to the CT image 800 of a disease case similar to the disease case of the diagnostic target CT image 1500.

Similar Case Image Retrieval Processing Result

Figure 17:
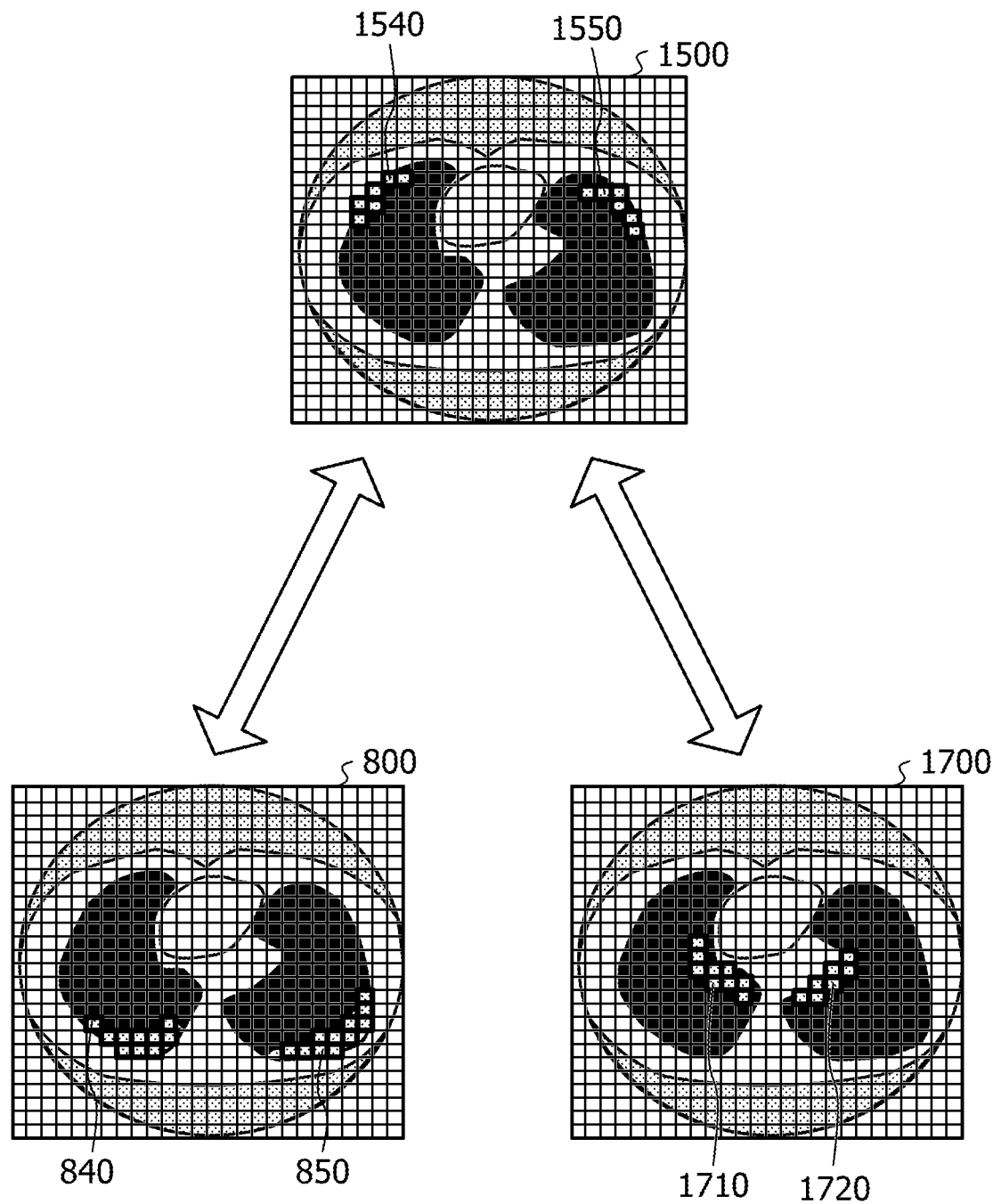
FIG. 17 is a diagram illustrating an example result of similar case image retrieval processing.

Next, the processing result of the similar case image retrieval processing will be described. FIG. 17 is a diagram illustrating an example result of similar case image retrieval processing. In FIG. 17, the CT image 1500 is a diagnostic target CT image, and the CT image 800 and CT image 1700 are those CT images for which a distribution characteristic quantity is registered in the characteristic quantity information DB 150 by the registration section 141.

As illustrated in FIG. 17, in the case of the diagnostic target CT image 1500, the blocks of abnormal shadow (for instance, the blocks 1540, 1550) are distributed over the peripheral portion in the lung regions. Also, in the CT image 800 out of the CT images for which a distribution characteristic quantity is registered by the registration section 141, the blocks of abnormal shadow (for instance, the blocks 840, 850) are distributed over the peripheral portion in the lung regions. In contrast, in the CT image 1700, the blocks of abnormal shadow (for instance, the blocks 1710, 1720) are distributed over the central portion in the lung regions.

Here, let D10 be the distance between the blocks (for instance, the blocks 1540, 1550) of abnormal shadows extracted from the diagnostic target CT image 1500, and the blocks (for instance, the blocks 840, 850) of abnormal shadows extracted from the CT image 800. That is, the distance D10 is the distance calculated based on the positions of the blocks of abnormal shadow on the CT image.

In addition, let D20 be the distance between the blocks (for instance, the blocks 1540, 1550) of abnormal shadows extracted from the diagnostic target CT image 1500, and the blocks (for instance, the blocks 1710, 1720) of abnormal shadows extracted from the CT image 1700. That is, the distance D20 is the distance calculated based on the positions of the blocks of abnormal shadow on the CT image.

When the distance D10 is compared with the distance D20, the distance D20 is shorter. In other words, the positions of blocks of abnormal shadow in the CT image 1500 are similar to the positions of blocks of abnormal shadow in the CT image 1700 than the positions of blocks of abnormal shadow in the CT image 800. For this reason, when a degree of similarity is calculated based on the positions on each CT image, a higher degree of similarity is calculated for the CT image 1700, and the CT image 800 is not retrieved as a CT image of a similar case.

Here, although the blocks of abnormal shadow on the CT image 1500 and the blocks of abnormal shadow on the CT image 1700 are distributed at relatively close positions, the former is an abnormal shadow occurred in the peripheral portion, and the latter is an abnormal shadow occurred in the central portion. That is, both are abnormal shadows with organizationally different occurrence portions, and are not CT images of a similar case.

In contrast, although the blocks of abnormal shadow on the CT image 1500 and the blocks of abnormal shadow on the CT image 800 are distributed at relatively far positions, both are abnormal shadows occurred in the peripheral portion. That is, both are abnormal shadows with organizationally the same occurrence portions, and are CT images of a similar case.

Here, in the case of the similar case image retrieval apparatus 120 in the first embodiment, a distribution characteristic quantity is calculated after each block is mapped so that the distance between the central portion and the peripheral portion becomes greater than the distance in the original CT image. In other words, a distribution characteristic quantity is calculated after the CT image is mapped so that abnormal shadows with organizationally different occurrence portions become more identifiable.

Consequently, the distribution characteristic quantity of the CT image 1500 and the distribution characteristic quantity of the CT image 800 become similar, and thus a total degree of similarity D calculated based on the both is increased. In contrast, the distribution characteristic quantity of the CT image 1500 and the distribution characteristic quantity of the CT image 1700 become dissimilar, and thus a total degree of similarity D' calculated based on the both is decreased. Accordingly, the CT image 800 is retrieved a CT image of a similar case.

As is apparent from the above description, in the case of diffuse lung disease, it is difficult to retrieve a CT image of a similar case based on similarity/dissimilarity of positions on a CT image. However, the similar case image retrieval apparatus 120 maps a CT image to an image having a predetermined shape and calculates the position (distribution characteristic quantity) of an abnormal shadow from an organizational viewpoint for occurrence portions, and retrieves a CT image using the distribution characteristic quantity. Thus, the similar case image retrieval apparatus 120 in the first embodiment may provide a retrieval technology capable of retrieving a CT image of a similar case for diffuse lung disease.

Second Embodiment

In the first embodiment, it has been described that each block in a CT image is mapped to a rectangular image. However, a destination of the mapping is not limited to a rectangular image.

Figure 18A:
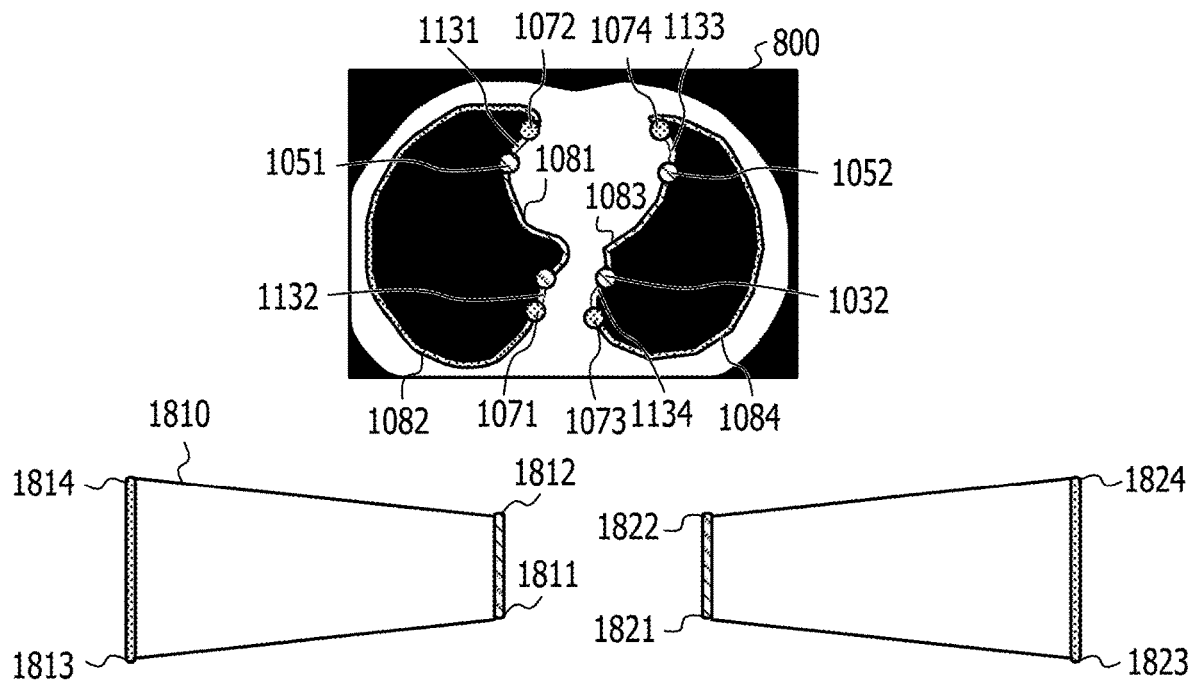
FIGS. 18A and 18B are each a diagram illustrating another example of nonlinear mapping processing performed by the distribution conversion section.
Figure 18B:
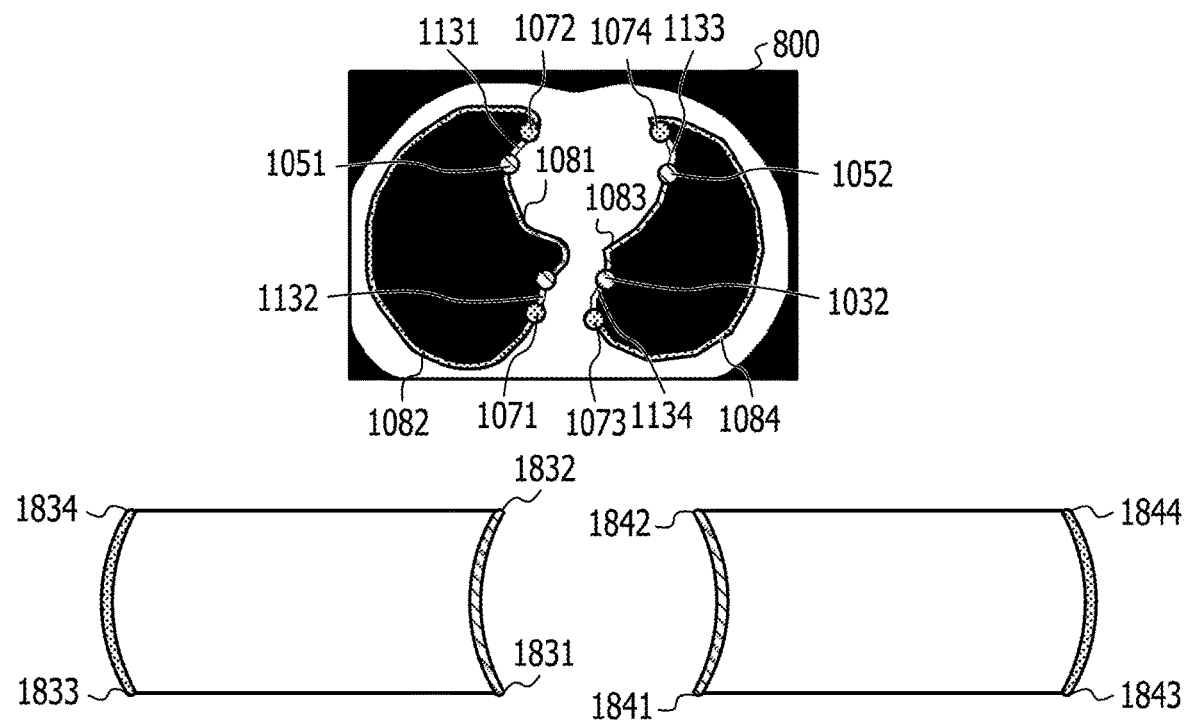

FIGS. 18A and 18B are each a diagram illustrating another example of nonlinear mapping processing performed by the distribution conversion section. The example of FIG. 18A illustrates the case where each block in a CT image is mapped to a trapezoidal image. In the case of FIG. 18A, the nonlinear mapping section 723 maps the contour 1081 extracted by the boundary point extraction section 722 so that the boundary points 1031, 1051 indicating both ends of the central portion correspond to two vertices 1811, 1812 of the contour of a trapezoidal image 1810. Also, the nonlinear mapping section 723 maps the contour 1082 extracted by the boundary point extraction section 722 so that the boundary points 1071, 1072 indicating both ends of the peripheral portion correspond to two vertices 1813, 1814 of the contour of the trapezoidal image 1810.

It is to be noted that for the mapping, the nonlinear mapping section 723 extracts sample points at regular intervals from the contours 1081, 1082, and performs mapping so that mapped sample points are arranged at regular intervals.

Also, the nonlinear mapping section 723 maps the contour 1083 extracted by the boundary point extraction section 722 so that the boundary points 1032, 1052 indicating both ends of the central portion correspond to two vertices 1821, 1822 of the contour of a trapezoidal image 1820. Also, the nonlinear mapping section 723 maps the contour 1084 extracted by the boundary point extraction section 722 so that the boundary points 1073, 1074 indicating both ends of the peripheral portion correspond to two vertices 1823, 1824 of the contour of the trapezoidal image 1820.

It is to be noted that for the mapping, the nonlinear mapping section 723 extracts sample points at regular intervals from the contours 1083, 1084, and performs mapping so that mapped sample points are arranged at regular intervals.

Also, the nonlinear mapping section 723 maps the contour 1131 extracted from the boundary point extraction section 722 so that the boundary points 1051, 1072 correspond to the two vertices 1812, 1814 of the contour of the trapezoidal image 1810. Also, the nonlinear mapping section 723 maps the contour 1132 extracted from the boundary point extraction section 722 so that the boundary points 1031, 1071 correspond to the two vertices 1811, 1813 of the contour of the trapezoidal image 1810.

It is to be noted that for the mapping, the nonlinear mapping section 723 extracts sample points at regular intervals from the contours 1131, 1132, and performs mapping so that mapped sample points are arranged at regular intervals.

Also, the nonlinear mapping section 723 maps the contour 1133 extracted from the boundary point extraction section 722 so that the boundary points 1052, 1074 correspond to the two vertices 1822, 1824 of the contour of the trapezoidal image 1820. Also, the nonlinear mapping section 723 maps the contour 1134 extracted from the boundary point extraction section 722 so that the boundary points 1032, 1073 correspond to the two vertices 1821, 1823 of the contour of the trapezoidal image 1820.

The example of FIG. 18B illustrates the case where each block in a CT image is mapped to an image having a predetermined shape surrounded by two curves and two straight lines. In the case of FIG. 18B, the nonlinear mapping section 723 maps the contour 1081 extracted by the boundary point extraction section 722 so that the boundary points 1031, 1051 indicating both ends of the central portion correspond to two vertices 1831, 1832 of the contour of an image 1830 having a predetermined shape.

Also, the nonlinear mapping section 723 maps the contour 1082 extracted by the boundary point extraction section 722 so that the boundary points 1071, 1072 indicating both ends of the peripheral portion correspond to two vertices 1833, 1834 of the image 1830 having a predetermined shape.

It is to be noted that for the mapping, the nonlinear mapping section 723 extracts sample points at regular intervals from the contours 1081, 1082, and performs mapping so that mapped sample points are arranged at regular intervals.

Also, the nonlinear mapping section 723 maps the contour 1083 extracted by the boundary point extraction section 722 so that the boundary points 1032, 1052 indicating both ends of the central portion correspond to two vertices 1841, 1842 of the contour of an image 1840 having a predetermined shape. Also, the nonlinear mapping section 723 maps the contour 1084 extracted by the boundary point extraction section 722 so that the boundary points 1073, 1074 indicating both ends of the peripheral portion correspond to two vertices 1843, 1844 of the contour of an image 1840 having a predetermined shape.

It is to be noted that for the mapping, the nonlinear mapping section 723 extracts sample points at regular intervals from the contours 1083, 1084, and performs mapping so that mapped sample points are arranged at regular intervals.

Also, the nonlinear mapping section 723 maps the contour 1131 extracted from the boundary point extraction section 722 so that the boundary points 1051, 1072 correspond to the two vertices 1832, 1834 of the contour of the trapezoidal image 1830. Also, the nonlinear mapping section 723 maps the contour 1132 extracted from the boundary point extraction section 722 so that the boundary points 1031, 1071 correspond to the two vertices 1831, 1833 of the contour of the trapezoidal image 1830.

It is to be noted that for the mapping, the nonlinear mapping section 723 extracts sample points at regular intervals from the contours 1131, 1132, and performs mapping so that mapped sample points are arranged at regular intervals.

Also, the nonlinear mapping section 723 maps the contour 1133 extracted from the boundary point extraction section 722 so that the boundary points 1052, 1074 correspond to the two vertices 1842, 1844 of the contour of the trapezoidal image 1840. Also, the nonlinear mapping section 723 maps the contour 1134 extracted from the boundary point extraction section 722 so that the boundary points 1032, 1073 correspond to the two vertices 1841, 1843 of the contour of the trapezoidal image 1840.

Like this, as long as each image at a mapping destination has a shape capable of identifying whether abnormal shadows distributed in a CT image are distributed over the central portion in the lung regions or the peripheral portion in the lung regions, the same effect as in mapping of an image to a rectangular image is achieved. Specifically, retrieval may be made using the positions (distribution characteristic quantities) of abnormal shadows calculated from an organizational viewpoint for occurrence portions, thus it is possible to provide a retrieval technology capable of retrieving a CT image of a similar case for diffuse lung disease.

OTHER EMBODIMENTS

In the first and second embodiments, although the aspect ratio of a predetermined shaped image to which a block in a CT image is mapped has not been particularly mentioned, any aspect ratio is applicable as long as the aspect ratio satisfies "the vertical length<the horizontal length".

Also, in the first and second embodiments, it has been described that the contour of each of the central portion and the peripheral portion is mapped to a vertical fixed contour which is part of the contour of an image having a predetermined shape. However, the contour of each of the central portion and the peripheral portion may be mapped to a horizontal fixed contour which is part of the contour of an image having a predetermined shape. This is because the same effect is achieved when the contour of the central portion and the contour of the peripheral portion are mapped to fixed contours at opposed positions. However, in this case, the aspect ratio of a predetermined shaped image has to satisfy "the vertical length>the horizontal length".

Also, in the first and second embodiments, the example has been described, in which the characteristic quantity information 500 and the CT image information 600 are stored in different DBs. However, the characteristic quantity information 500 and the CT image information 600 may be stored in the same DB.

Also, in the first and second embodiments, it has been described that a distribution characteristic quantity for the diagnostic target CT image 1500 is calculated after a retrieval instruction is received. However, the distribution characteristic quantity of the diagnostic target CT image 1500 may be calculated before a retrieval instruction is received.

Also, in the first and second embodiments, an example of application to a CT image of diffuse lung disease has been described. However, application to a CT image of a disease of an internal organ other than the lung is possible for diffuse lung disease.

Also, in the first and second embodiments, the example has been described, in which a CT image is displayed as a medical image. However, the present disclosure is applicable to the case where a medical image other than a CT image (for instance, a magnetic resonance imaging (MRI) image) is displayed.

It is to be noted that the configuration described in the embodiments may be combined with other components, and the present disclosure is not limited to the configuration presented herein. Regarding these points, modifications may be made without departing from the spirit of the present disclosure, and setting may be appropriately made according to an application configuration.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. An image retrieval apparatus that retrieves a candidate medical image in diagnosis of diffuse lung disease based on a position of an abnormal shadow in an organ region in a target medical image, the apparatus comprising:
    a memory; and
    a processor coupled to the memory and configured to:
    map the organ region in the target medical image to an image such that a contour of the organ region is changed to a geometric shape to make it identifiable whether the abnormal shadow is distributed over a first portion in the organ region or a second portion in the organ region, occurrence portions of the abnormal shadow within the first portion and the second portion are different; and
    calculate a position of the abnormal shadow after the mapping in the image having the geometric shape,
    wherein a first contour that is of a contour of the organ region and corresponds to the first portion is mapped to a first fixed contour that is part of a contour of the image having the geometric shape, and a second contour that corresponds to the second portion is mapped to a second fixed contour at a position opposed to the first contour, out of the contour of the image having the geometric shape,
    wherein out of reduced contours obtained by reducing the contour of the organ region, a first reduced contour corresponding to the first portion is mapped to a first reduced fixed contour that is part of a reduced contour obtained by reducing the contour of the image having the geometric shape, and a second reduced contour corresponding to the second portion is mapped to a second reduced fixed contour at a position opposed to the first reduced fixed contour, out of the reduced contour obtained by reducing the contour of the image having the geometric shape,
    wherein a region between nth reduced contour obtained by reducing the contour of the organ region by a first ratio, and (n+1)th reduced contour obtained by reducing the contour of the organ region by a second ratio higher than the first ratio is mapped to the image having the geometric shape so that a positional relationship between the nth reduced contour and the (n+1)th reduced contour is maintained.

2. The image retrieval apparatus according to claim 1, wherein the organ region in the target medical image is mapped so that a distance between the first portion and the second portion is a predetermined value or greater.

3. The image retrieval apparatus according to claim 1, wherein based on first coordinates that, when the organ region in the target medical image which is a diagnostic target is mapped to the image having the geometric shape, indicate a position of the abnormal shadow in the organ region in the image having the geometric shape, and second coordinates that, when an organ region in the candidate medical image which is a retrieval target is mapped to the image having the geometric shape, indicate a position of the abnormal shadow in the organ region in the image having the geometric shape, a medical image similar to the medical image which is the diagnostic target is retrieved from the medical image which is the retrieval target.

4. The image retrieval apparatus according to claim 3, wherein the candidate medical image, which is similar to the target medical image is retrieved based on a distance between the first coordinates and the second coordinates.

5. The image retrieval apparatus according to claim 4, wherein the organ region is a lung region, and the candidate medical image similar to the target medical image is retrieved based on a total value of the distance between the first coordinates and the second coordinates calculated for a right lung, and the distance between the first coordinates and the second coordinates calculated for a left lung.

6. The image retrieval apparatus according to claim 1, wherein a region between the contour of the organ region and the reduced contour obtained by reducing the contour of the organ region by a predetermined ratio is mapped to the image having the geometric shape so that a positional relationship between the contour and the reduced contour is maintained.

7. The image retrieval apparatus according to claim 1, wherein the processor is further configured to:
   obtain a position of the abnormal shadow of the candidate medical image; and
   determine a similarity between the candidate medical image and the target medical image based on the calculated position associated with the target medical image and the obtained position associated with the candidate medical image.

8. A computer-implemented image retrieval method that retrieves a candidate medical image in diagnosis of diffuse lung disease based on a position of an abnormal shadow in an organ region in a target medical image,
   the method comprising:
   mapping, by a processor, the organ region in the target medical image to an image such that a contour of the organ region is changed to a geometric shape to make it identifiable whether the abnormal shadow is distributed over a first portion in the organ region or a second portion in the organ region, occurrence portions of the abnormal shadow within the first portion and the second are different; and
   calculating, by a processor, a position of the abnormal shadow after the
   mapping in the image having the geometric shape,
   wherein a first contour that is of a contour of the organ region and corresponds to the first portion is mapped to a first fixed contour that is part of a contour of the image having the geometric shape, and a second contour that corresponds to the second portion is mapped to a second fixed contour at a position opposed to the first contour, out of the contour of the image having the geometric shape,
   wherein out of reduced contours obtained by reducing the contour of the organ region, a first reduced contour corresponding to the first portion is mapped to a first reduced fixed contour that is part of a reduced contour obtained by reducing the contour of the image having the geometric shape, and a second reduced contour corresponding to the second portion is mapped to a second reduced fixed contour at a position opposed to the first reduced fixed contour, out of the reduced contour obtained by reducing the contour of the image having the geometric shape,
   wherein a region between nth reduced contour obtained by reducing the contour of the organ region by a first ratio, and (n+1)th reduced contour obtained by reducing the contour of the organ region by a second ratio higher than the first ratio is mapped to the image having the predetermined geometric shape so that a positional relationship between the nth reduced contour and the (n+1)th reduced contour is maintained.

9. A medical image retrieval system comprising:
   a database configured to store a plurality of characteristic quantity information associated with a plurality of medical images;
   a processor configured to
   obtain a target medical image for diagnosis of diffuse lung disease based on a position of an abnormal shadow in an organ region of the target medical image, the organ region including at least a first portion and a second portion having different positions with respect to a reference point;
   identifying occurrence portions of the abnormal shadow within at least one of the first portion and the second portion of the target medical image;
   map the organ region of the target medical image to an image having a geometric shape;
   calculate a target characteristic quantity of the occurrence portions based on the image having the geometric shape and the identified occurrence portions; and
   retrieve a candidate medical image from the database based on the calculated target characteristic quantity, the candidate medical image having occurrence portions similar to the target medical image,
   wherein a first contour that is of a contour of the organ region and corresponds to the first portion is mapped to a first fixed contour that is part of a contour of the image having the geometric shape, and a second contour that corresponds to the second portion is mapped to a second fixed contour at a position opposed to the first contour, out of the contour of the image having the geometric shape,
   wherein out of reduced contours obtained by reducing the contour of the organ region, a first reduced contour corresponding to the first portion is mapped to a first reduced fixed contour that is part of a reduced contour obtained by reducing the contour of the image having the geometric shape, and a second reduced contour corresponding to the second portion is mapped to a second reduced fixed contour at a position opposed to the first reduced fixed contour, out of the reduced contour obtained by reducing the contour of the image having the geometric shape,
   wherein a region between nth reduced contour obtained by reducing the contour of the organ region by a first ratio, and (n+1)th reduced contour obtained by reducing the contour of the organ region by a second ratio higher than the first ratio is mapped to the image having the predetermined geometric shape so that a positional relationship between the nth reduced contour and the (n+1)th reduced contour is maintained.

* * * * *